United States Patent
Palermo et al.

(10) Patent No.: US 12,251,263 B2
(45) Date of Patent: Mar. 18, 2025

(54) DEVICES, SYSTEMS, AND METHODS FOR AUTOMATED DELAY DETECTION BETWEEN MEDICAL-IMAGING DEVICES

(71) Applicant: Canon U.S.A., Inc., Melville, NY (US)

(72) Inventors: Justin Hotchkiss Palermo, Boston, MA (US); Daisuke Yamada, Cambridge, MA (US); James Hastings Houskeeper, Mendon, MA (US)

(73) Assignee: Canon U.S.A., Inc., Melville, NY (US)

( * ) Notice: Subject to any disclaimer, the term of this patent is extended or adjusted under 35 U.S.C. 154(b) by 71 days.

(21) Appl. No.: 17/831,018

(22) Filed: Jun. 2, 2022

(65) Prior Publication Data

US 2023/0389892 A1 Dec. 7, 2023

(51) Int. Cl.
*A61B 8/00* (2006.01)
*A61B 6/00* (2024.01)
*A61B 8/08* (2006.01)

(52) U.S. Cl.
CPC .......... *A61B 8/4416* (2013.01); *A61B 6/4417* (2013.01); *A61B 8/5207* (2013.01); *A61B 6/5247* (2013.01); *A61B 8/54* (2013.01)

(58) Field of Classification Search
CPC ... A61B 8/4416; A61B 6/4417; A61B 8/5207; A61B 6/5247; A61B 8/54; A61B 6/487; A61B 6/486; A61B 8/5261; A61B 8/565; A61B 5/0095; A61B 8/12
See application file for complete search history.

(56) References Cited

U.S. PATENT DOCUMENTS

| | | | |
|---|---|---|---|
| 3,528,731 A | 9/1970 | Bird | |
| 8,565,859 B2 | 10/2013 | Wang | |
| 2004/0081278 A1* | 4/2004 | Amemiya | A61B 6/466 378/63 |
| 2008/0177183 A1* | 7/2008 | Courtney | A61B 1/00112 600/463 |
| 2012/0059253 A1* | 3/2012 | Wang | A61B 6/5247 600/427 |
| 2013/0245445 A1* | 9/2013 | Kakee | A61B 8/5276 600/443 |
| 2015/0173698 A1* | 6/2015 | Sakaguchi | A61B 8/466 378/62 |
| 2016/0073885 A1* | 3/2016 | Adler | A61B 5/0066 600/427 |
| 2020/0286237 A1* | 9/2020 | Butler | G06T 7/0016 |

FOREIGN PATENT DOCUMENTS

KR 20220106811 A * 11/2020

* cited by examiner

*Primary Examiner* — Baisakhi Roy
*Assistant Examiner* — Kaitlyn E Sebastian
(74) *Attorney, Agent, or Firm* — Canon U.S.A., Inc. IP Division

(57) ABSTRACT

Devices, systems, and methods obtain first imaging data and first timestamps that correspond to the first imaging data; obtain second imaging data and second timestamps that correspond to the second imaging data; demodulate the first imaging data to acquire a first timing signal; demodulate the second imaging data to acquire a second timing signal; and calculate a delay value based on the first timing signal, the second timing signal, the first timestamps, and the second timestamps.

20 Claims, 20 Drawing Sheets

DEVICES, SYSTEMS, AND METHODS FOR AUTOMATED DELAY DETECTION BETWEEN MEDICAL-IMAGING DEVICES

BACKGROUND

Technical Field

This application generally concerns devices, systems, and methods that perform medical imaging.

Background

Bendable optical-imaging devices (e.g., endoscopes, flexible borescopes) enable the imaging of internal tissues, organs, and structures. For example, in cardiology, a bendable optical-imaging device that is capable of optical coherence tomography (OCT) may be used to acquire depth-resolved images of a sample (e.g., tissues, organs). Additionally, some bendable optical-imaging devices use fluorescence imaging, such as near-infrared fluorescence ("NIRF") (e.g., near-infrared autofluorescence ("NIRAF")). Fluorescence imaging enables the visualization of molecular processes (e.g., biological processes in an organism). The bendable optical-imaging device, which may include a flexible body, a coil, and an optical probe, may be navigated through a lumen (e.g., a vessel) or a cavity.

Also, radiographic systems (e.g., medical radiographic systems, industrial radiographic systems) can generate images of the internal structures of objects. For example, to create an image of an object in X-ray radiography (e.g., during an angiography), a beam of X-rays is generated by an X-ray generator and is projected toward the object. Some of the X-rays are absorbed by the object, depending on the object's density and structural composition, and some of the X-rays pass through the object. The X-rays that have passed through the object are detected by a detector, which generates signals that can be used to generate images of the object.

SUMMARY

Some embodiments of a device comprise one or more computer-readable media storing instructions and one or more processors that are in communication with the one or more computer-readable media. Also, when executing the instructions, the one or more processors cooperate with the one or more computer-readable media to cause the device to perform operations that comprise obtaining first imaging data and first timestamps that correspond to the first imaging data; obtaining second imaging data and second timestamps that correspond to the second imaging data; demodulating the first imaging data to acquire a first timing signal; demodulating the second imaging data to acquire a second timing signal; and calculating a delay value based on the first timing signal, the second timing signal, the first timestamps, and the second timestamps.

Some embodiments of a system comprise a light source; a shutter; one or more computer-readable media storing instructions; and one or more processors that are in communication with the one or more computer-readable media. Also, when executing the instructions, the one or more processors cooperate with the one or more computer-readable media to cause the system to perform operations that comprise controlling the light source to emit light such that the light encodes a first transmitted timing signal; and controlling the shutter such that X-rays that travel through the shutter encode a second transmitted timing signal.

Some embodiments of a method comprise obtaining first imaging data and first timestamps that correspond to the first imaging data; obtaining second imaging data and second timestamps that correspond to the second imaging data; demodulating the first imaging data to acquire a first timing signal; demodulating the second imaging data to acquire a second timing signal; and calculating a delay value based on the first timing signal, the second timing signal, the first timestamps, and the second timestamps.

Some embodiments of a system comprise a light source; one or more computer-readable media storing instructions; and one or more processors that are in communication with the one or more computer-readable media. Also, when executing the instructions, the one or more processors cooperate with the one or more computer-readable media to cause the system to perform operations that comprise controlling the light source to emit light such that the light encodes a first transmitted timing signal; obtaining first imaging data and first timestamps that correspond to the first imaging data; obtaining second imaging data and second timestamps that correspond to the second imaging data; demodulating the first imaging data to acquire a first timing signal; demodulating the second imaging data to acquire a second timing signal; and calculating a delay value based on the first timing signal, the second timing signal, the first timestamps, and the second timestamps.

DESCRIPTION

Figure 1:
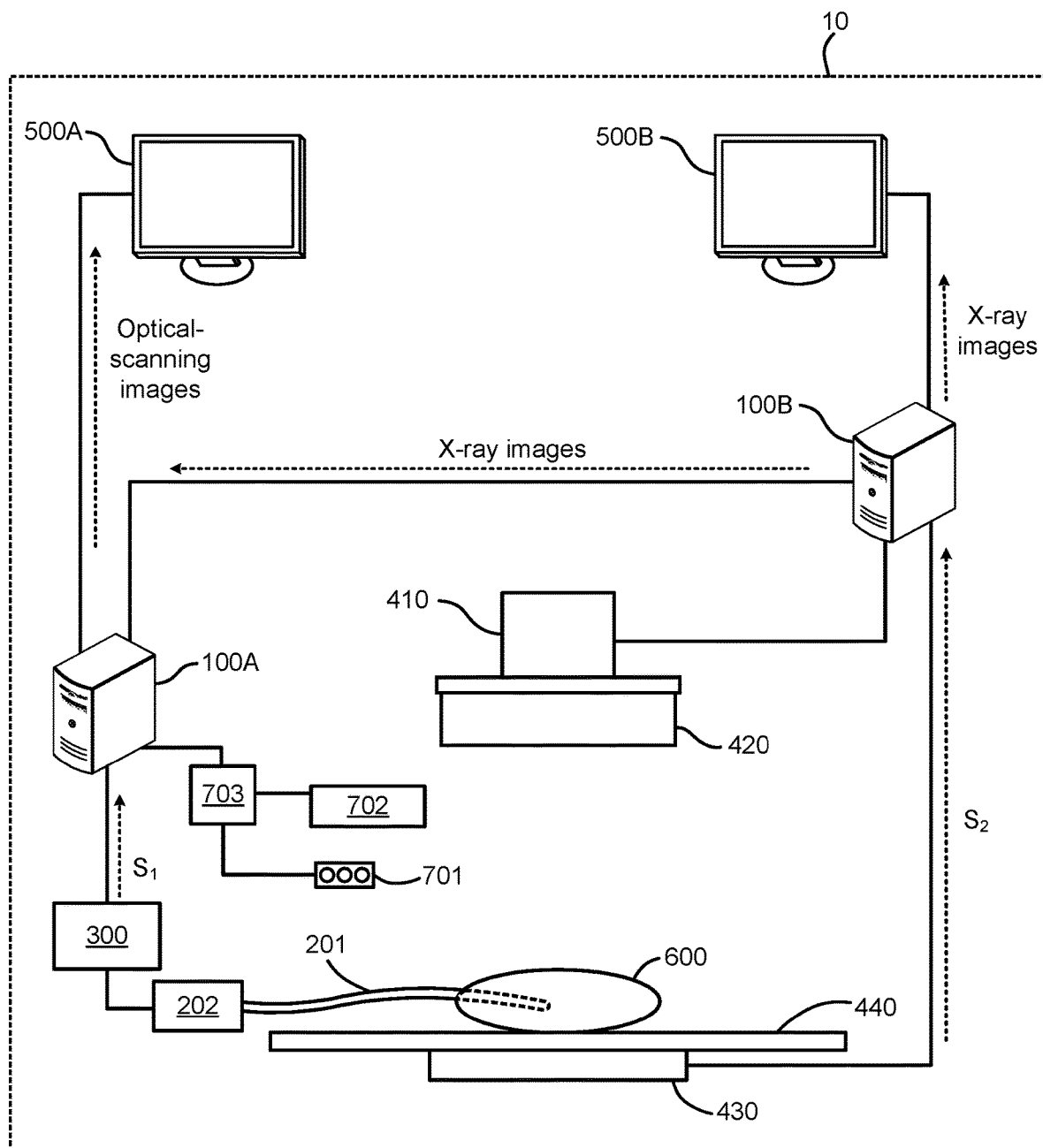
FIG. 1 is a schematic of an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation and may be used to distinguish one member, operation, element, group, collection, set, etc. from another without expressing any ordinal, sequential, or priority relation.

And, in the following description and in the drawings, like reference numerals designate identical, similar, or corresponding features. Also, an alphabetic suffix on a reference numeral may be used to indicate a specific instance of the feature identified by the reference numeral. For example, the imaging stations in a group of two or more imaging stations may be identified with the reference numeral 100 when a particular imaging station is not being distinguished. However, 100A may be used to identify a specific imaging station when the specific imaging station is being distinguished from the rest of the imaging stations 100.

Figure 2:
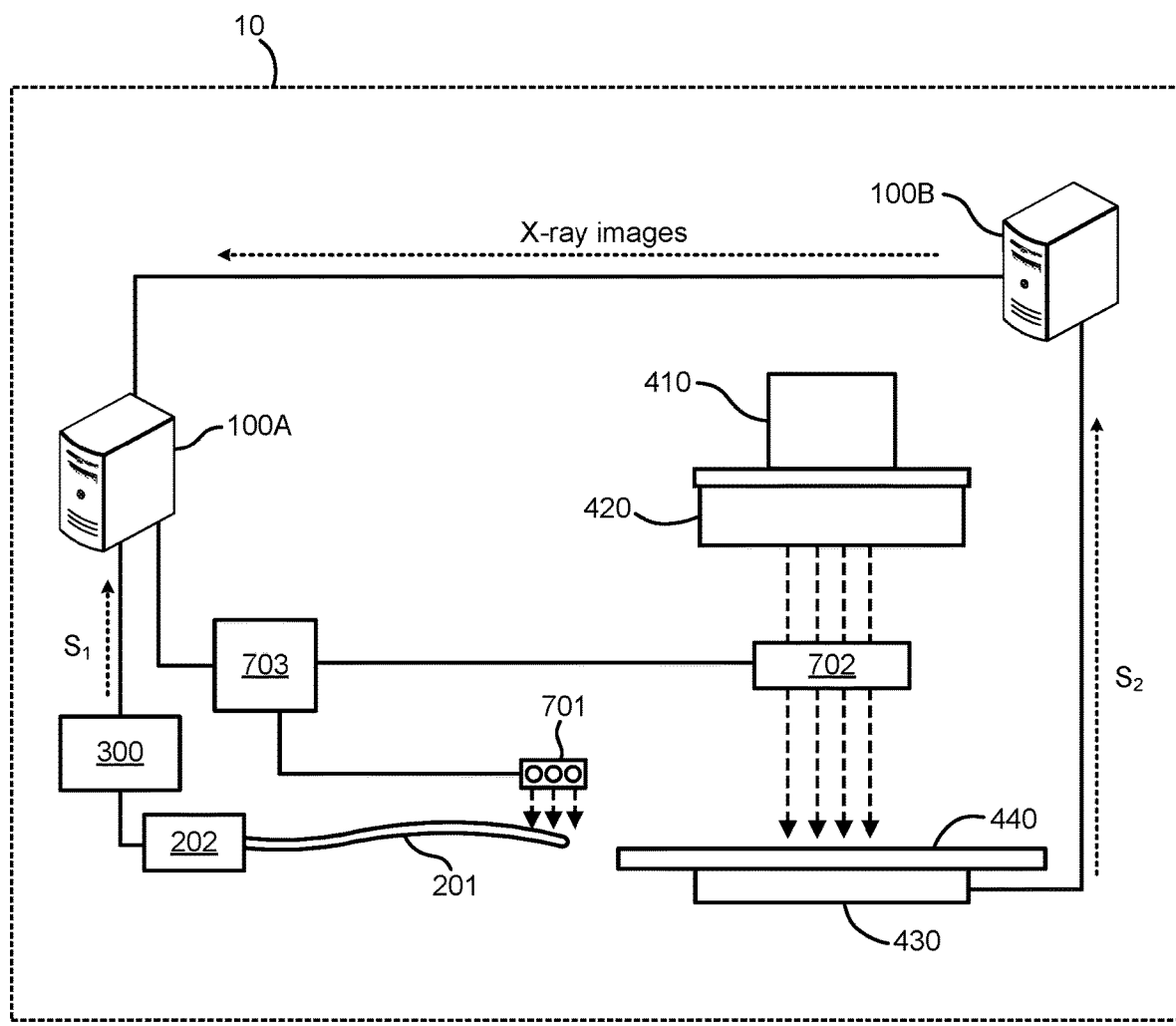
FIG. 2 is a schematic of an example embodiment of a medical-imaging system.

FIG. 1 is a schematic of an example embodiment of a medical-imaging system 10. Also, FIG. 2 illustrates the medical-imaging system 10 during a delay-calculation procedure. The medical-imaging system 10 includes at least two imaging stations 100, which are specially-configured computing devices (e.g., desktops, laptops, servers, workstations); a bendable optical-imaging device 201; a patient-interface unit (PIU) 202; a probe-interface subsystem 300; an X-ray generator 410; a beam-control device 420; an X-ray detector 430; a support surface 440; at least two display devices 500; an external light source 701 (e.g., one or more LED bulbs); an external shutter 702; and a timing-and-synchronization circuit 703.

The bendable optical-imaging device 201 can perform optical-scanning procedures inside a lumen (e.g., vessel, bronchus, intestine, trachea, ear canal), cavity (e.g., stomach, nasal cavity) or other structure. In FIG. 1, the bendable optical-imaging device 201 extends into a lumen of a patient 600. During an optical-scanning procedure, the probe-interface subsystem 300 generates light (e.g., OCT light, excitation light) and supplies the generated light to the bendable optical-imaging device 201. The bendable optical-imaging device 201 carries the light (e.g., OCT light, excitation light) to a distal end, where the light is emitted. And, at the distal end, the bendable optical-imaging device 201 collects light (e.g., OCT light, fluorescence light) that is emitted or reflected by the lumen of the patient 600.

Figure 4:
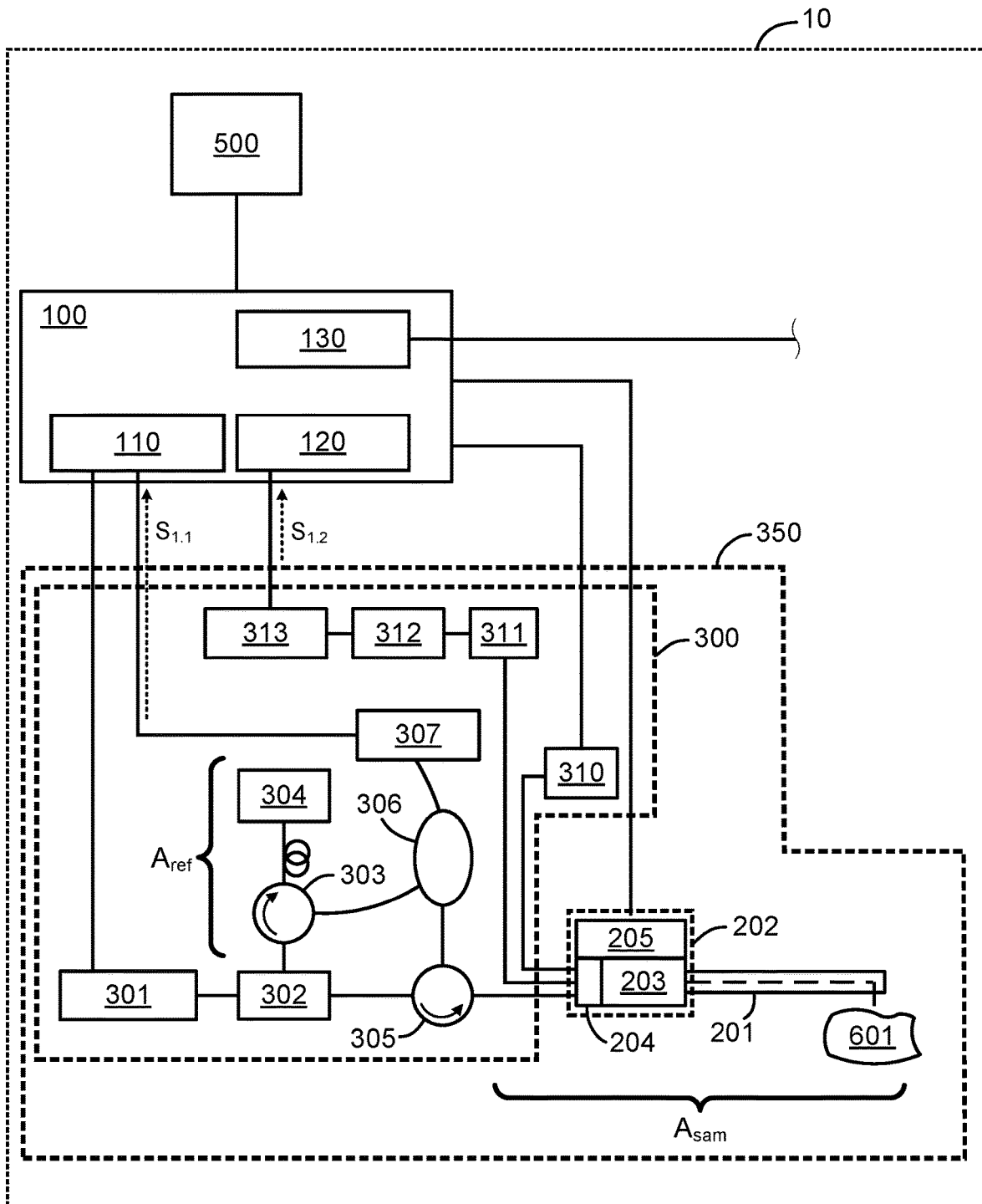
FIG. 4 is a schematic of an example embodiment of a medical-imaging system that illustrates additional details of a probe-interface subsystem.

The collected light is carried from the distal end of the bendable optical-imaging device 201, through the PIU 202, to the probe-interface subsystem 300. Based on the received light, the probe-interface subsystem 300 generates first detection signals $S_1$, which carry first detection data (e.g., a series of first detection data, such as a series of groups of first detection data), and supplies the first detection signals $S_1$ to a first imaging station 100A. The first detection signals $S_1$ may include multiple modalities of detection signals, for example OCT-detection signals $S_{1.1}$ (e.g., as shown in FIG. 4) and fluorescence-detection signals $S_{1.2}$ (e.g., as shown in FIG. 4). Accordingly, the first detection data may include, for example, OCT-detection data or fluorescence-detection data.

Based on the first detection data, the first imaging station 100A generates one or more optical-scanning images (e.g., a series of optical-scanning images). For example, each optical-scanning image in a series of optical-scanning images may be generated from a respective group of first detection data in a series of groups of first detection data. The first imaging station 100A supplies the one or more optical-scanning images to a first display device 500A, which displays the one or more optical-scanning images. For example, the first imaging station 100A may generate a user interface that includes the one or more optical-scanning images and transmit the user interface to the first display device 500A. Also, examples of optical-scanning images include the following: OCT images, fluorescence images, and multi-modal images (e.g., an OCT-fluorescence image, such as a co-registered OCT-fluorescence image). Furthermore, in some embodiments, each optical-scanning image is formed by a set of frames in which each frame is a one-dimensional array of pixels.

And the first imaging station 100A may add respective timestamps (e.g., that indicate time of reception) to the first detection data as the first detection data are received (e.g., timestamps that respectively indicate when first detection data in a series of first detection data were received), and the first imaging station 100A may add timestamps to the one or more optical-scanning images as the one or more optical-scanning images are generated (e.g., timestamps that respectively indicate when the generation of each optical-scanning image in a series of optical-scanning images was completed).

Additionally, when active, the X-ray generator 410 emits X-rays toward the beam-control device 420. The beam-control device 420 controls the X-ray beams that travel through the beam-control device 420 toward the patient 600, the support surface 440, and the X-ray detector 430. The X-rays that pass through the patient 600 and the support surface 440 are detected by the X-ray detector 430, which generates second detection signals $S_2$ based on the detected X-rays and supplies the second detection signals $S_2$ to a second imaging station 100B. The second detection signals $S_2$ carry second detection data (e.g., a series of second detection data, such as a series of groups of second detection data). The second imaging station 100B generates one or more X-ray images (e.g., a series of X-ray images) of the patient 600 based on the second detection data. For example, each X-ray image in a series of X-ray images may be generated from a respective group of second detection data in a series of groups of second detection data. The second imaging station 100B sends the one or more X-ray images to a second display device 500B, which displays the X-ray images. Thus, for example, the X-ray generator 410, the beam-control device 420, and the X-ray detector 430 can be used to acquire angiographic images (e.g., fluoroscopic images), which are examples of X-ray images. Additionally, the second imaging station 100B sends the X-ray images to the first imaging station 100A. And the second imaging station 100B may add timestamps to the one or more X-ray images as the one or more X-ray images are generated (e.g., timestamps that respectively indicate when the generation of each X-ray image in a series of X-ray images was completed), or the first imaging station 100A may add respective timestamps (e.g., that indicate time of reception) to the X-ray images as the X-ray images are received (e.g., timestamps that respectively indicate when the reception of each X-ray image in a series of X-ray images was completed). Also, the timestamps that are added by the first imaging station 100A may be independent of the timestamps that are added by the second imaging station 100B, and thus the first imaging station 100A and the second imaging station 100B may not communicate about the timestamps.

In this example embodiment, the first imaging station 100A controls the bendable optical-imaging device 201, the PIU 202, and the probe-interface subsystem 300. And the second imaging station 100B controls the X-ray generator 410, the beam-control device 420, and the X-ray detector 430. Also, the first imaging station 100A controls the external light source 701, the external shutter 702, and the timing-and-synchronization circuit 703.

Examples of the external light source 701 (which is external to the optical probe 201) include one or more LEDs, such as an LED that emits light in wavelengths (e.g., 700 nm) that can be detected by an optical probe 201 that is configured for NIRAF detection. The external shutter 702 may include one or more actuators or one or more motors that can rapidly open and close the shutter 702. Also, the timing-and-synchronization circuit 703 may include one or more processors (e.g., microcontrollers) and may include oscillators (e.g., high precision temperature controlled oscillators) that activate the external light source 701 and that activate the external shutter 702. And some embodiments of the timing-and-synchronization circuit 703 include two timing circuits, one of which is attached to the output of the other, which prevents the first timing circuit from signaling again until the second circuit finishes its countdown. This may produce a steady rate of timing pulses. Also, the timing circuits can be adjusted with a digital potentiometer. The timing-and-synchronization circuit 703 can synchronize the external light source 701 and the external shutter 702 such that the timing signal carried in the light emitted by the external light source 701 is synchronized with the timing signal carried in the X-rays that travel through the external shutter 702.

When the probe-interface subsystem 300 and the X-ray detector 430 are simultaneously supplying the first detection signals $S_1$ and the second detection signals $S_2$ (e.g., during an angiography-guided endoscopy), the display of the optical-scanning images on the first display device 500A may not be synchronized with the display of the X-ray images on the second display device 500B, or the timings of the first detection signals $S_1$ and the second detection signals $S_2$ may not be synchronized. For example, an optical-scanning image that was captured at time t may not be displayed at the same time that an X-ray image that was captured at time t is displayed, but instead the optical-scanning image may be displayed at $t+d_{disp1}$ and the X-ray image may be displayed at time $t+d_{disp2}$, where $d_{disp1}$ and $d_{disp2}$ indicate respective delays, and where $d_{disp1} \neq d_{disp2}$. This relative delay may occur because of various reasons, for example differences in the computing power and hardware configurations of the first and second imaging stations 100 and differences in the computing resources required to generate optical-scanning images and X-ray images. Also, at least some of the first detection data (e.g., group of first detection data that define an optical-scanning image) that were captured at time t may not arrive at, or be received by, the first imaging station 100A at the same time that the second detection data (e.g., a group of detection data that define an X-ray image) that were captured at time t arrive at, or be received by, the second imaging station 100B (or, in some embodiments, at the first imaging station 100A), but instead the first detection data may arrive at the first imaging station 100A at time $t+d_{rec1}$ and the second detection data may arrive at the second imaging station 100B at time $t+d_{rec2}$, where $d_{rec1}$ and $d_{rec2}$ indicate respective delays, and where $d_{rec1} \neq d_{rec2}$.

Figure 3A:
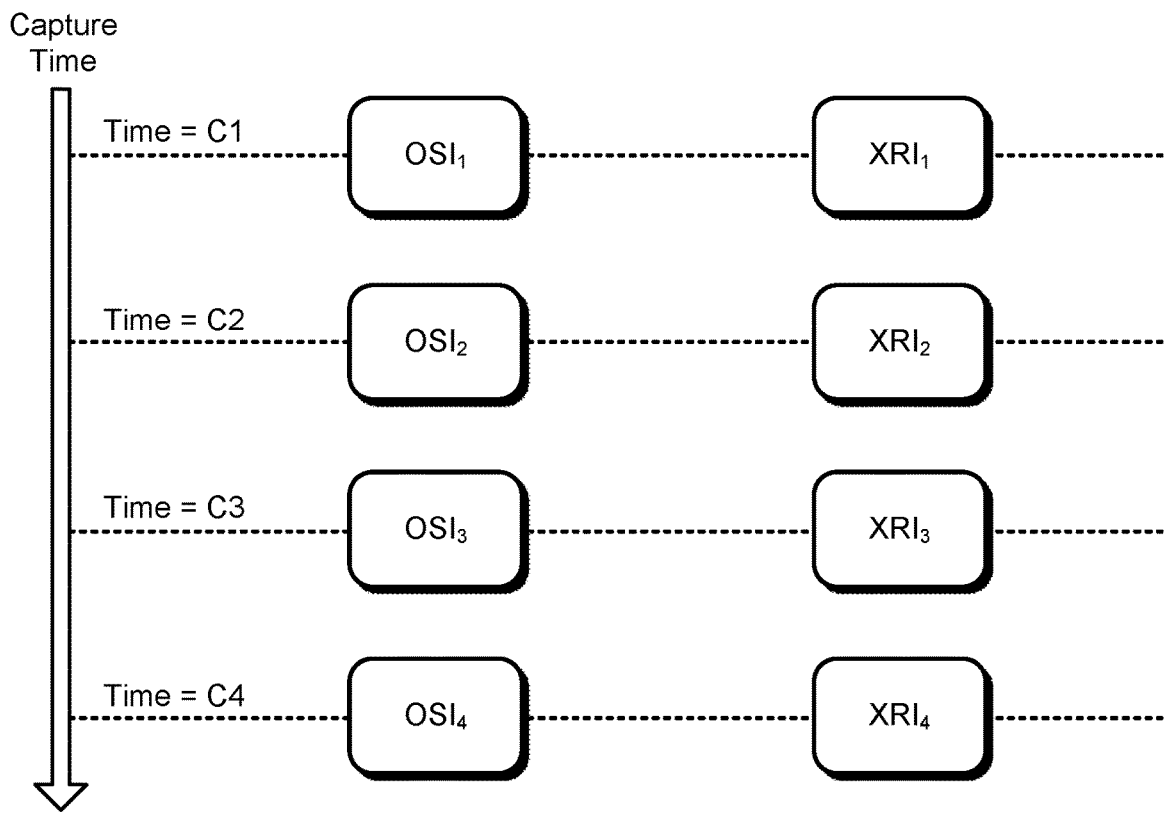
FIG. 3A illustrates examples of capture times of optical-scanning images and X-ray images.
Figure 3B:
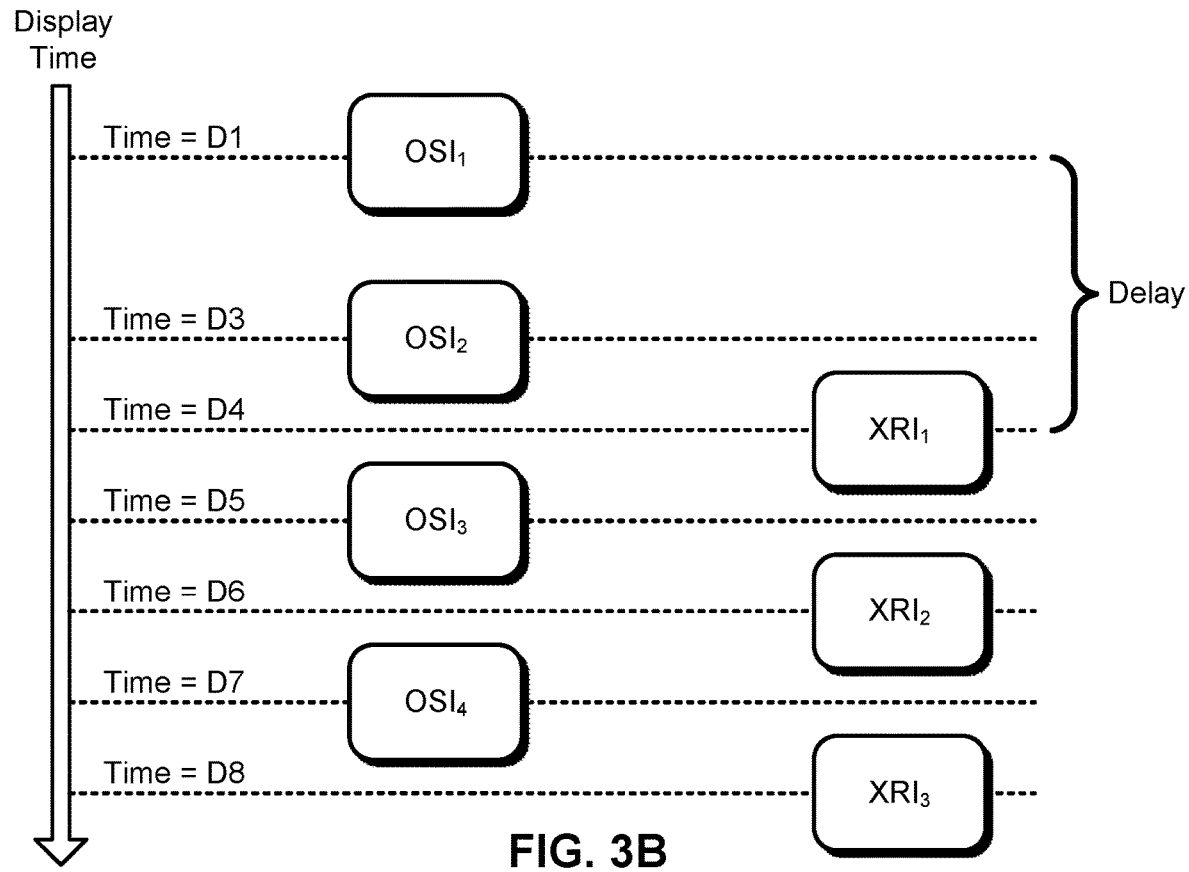
FIG. 3B illustrates examples of display times of optical-scanning images and X-ray images.

For example, FIG. 3A illustrates examples of capture times of optical-scanning images and X-ray images, and FIG. 3B illustrates examples of display times of optical-scanning images and X-ray images. The optical-scanning images in a series of optical-scanning images include optical-scanning image $OSI_1$, optical-scanning image $OSI_2$, optical-scanning image $OSI_3$, and optical-scanning image $OSI_4$. The X-ray images in a series of X-ray images include X-ray image $XRI_1$, X-ray image $XRI_2$, X-ray image $XRI_3$, and X-ray image $XRI_4$.

In FIG. 3A, optical-scanning image $OSI_1$ and X-ray image $XRI_1$ were captured at time C1. Note that this illustration is simplified for illustrative purposes. The capturing of the detection data that constitute these images was performed during a respective sampling period (e.g., during a respective sample-and-hold operation). Thus, for example, time C1 may indicate the beginning or the end of the sampling period, time C1 may indicate that the sampling period includes time C1, and time C1 may indicate a sampling period rather than an instant in time. Also in FIG. 3A, optical-scanning image $OSI_2$ and X-ray image $XRI_2$ were captured at time C2, optical-scanning image $OSI_3$ and X-ray image $XRI_3$ were captured at time C3, and optical-scanning image $OSI_4$ and X-ray image $XRI_4$ were captured at time C4.

FIG. 3B shows the display times of the images. Note that the time reference in FIG. 3B is different from FIG. 3A (i.e., time C1 in FIG. 3A is different from, and occurs before, time D1 in FIG. 3B). Although optical-scanning image $OSI_1$ was captured at the same time as X-ray image $XRI_1$, optical-scanning image $OSI_1$ is displayed from time=D1 to time=D3, and X-ray image $XRI_1$ is displayed from time=D4 to time=D6. Thus, there is a delay between the display of optical-scanning image $OSI_1$ and X-ray image $XRI_1$. For example, in a case where the first detection data that were captured at time t are displayed in an optical-scanning image (e.g., optical-scanning image $OSI_1$) at time $t+d_{disp1}$, and where the second detection data that were captured at time t are displayed in an X-ray image (e.g., X-ray image $XRI_1$) at time $t+d_{disp2}$, where $d_{disp2} > d_{disp1}$, then the delay between the display of the optical-scanning image and the X-ray image is equal to $d_{disp2} - d_{disp1}$.

In some embodiments, the delay is manifested in other ways. For example, in embodiments where the first detection data and the second detection data have timestamps (e.g., timestamps that indicate when the data were received by an imaging station), the first detection data that were captured at time t and the second detection data that were captured at time t may have different timestamps. In such embodiments, a group of the first detection data (e.g., data that define an optical-scanning image) may have a timestamp that indicates time $t+d_{rec1}$, and a group of the second detection data (e.g., data that define an X-ray image) that were captured at the same time may have a timestamp that indicates time t+$d_{rec2}$. Thus, the delay may be manifested in the different timestamps on first and second detection data that were captured at the same time.

Furthermore, in some imaging applications, synchronizing the display of the optical-scanning images and the X-ray images is advantageous. For example, while performing an angiography to guide the bendable optical-imaging device 201, synchronizing the display of the optical-scanning images and the X-ray images may assist a user in understanding the optical-scanning images by allowing the user to, based on the X-ray images, accurately register (e.g., identify the locations and orientations of) the bendable optical-imaging device 201 in a lumen at the times when the optical-scanning images were captured. Additionally, synchronizing the optical-scanning images and the X-ray images allows diagnostic information and user measurements made using the first detection data to be depicted on the corresponding image from the second detection data and vice versa.

Accordingly, the first imaging station 100A may perform a delay-calculation procedure to calculate a delay between the optical-scanning images and the X-ray images, between the first detection signals $S_1$ and the X-ray images, or between the first detection signals $S_1$ and the second detection signals $S_2$. For example, during a delay-calculation procedure (which, as shown in FIG. 2, can be performed while the optical probe 201 is not inside a lumen), the external light source 701, which emits light in wavelengths that can be detected by the optical probe 201, is positioned such that it emits light that is incident on the optical probe 201. Also, the external shutter 702, which is opaque to X-rays, is positioned between the beam-control device 420 and the X-ray detector 430. The timing-and-synchronization circuit 703 (e.g., in response to an instruction from the first imaging station 100A) controls the external light source 701 to repeatedly switch on and off and controls the external shutter 702 to repeatedly open and close. The light that is emitted by the external light source 701 is detected by the optical probe 201 and converted into first detection data that are supplied to the first imaging station 100A in the first signals $S_1$. Also, the X-rays that are emitted by the X-ray generator 410, that pass through the beam-control device 420, and that pass through the external shutter 702 are detected by the X-ray detector 430 and converted into second detection data, which are supplied to the second imaging station 100B in the second signals $S_2$. The second image station 100B generates one or more X-ray images based on the second signals $S_2$ and supplies the X-ray images to the first imaging station 100A.

The first imaging station 100A then calculates a delay value, which may indicate the delay between optical-scanning images and X-ray images. Also, once the first imaging station 100A has calculated the delay value, the first imaging station 100A may adjust the timing of the display of optical-scanning images on the first display device 500A according to the delay value so that the display of optical-scanning images is synchronized with the display of X-ray images (e.g., an optical-scanning image and an X-ray image that were both captured at time t are displayed simultaneously). Or the first imaging station 100A may send the delay value to the second imaging station 100B, which may then adjust the timing of the display of X-ray images on the second display device 500B according to the delay value so that the display of optical-scanning images is synchronized with the display of X-ray images.

FIG. 4 is a schematic of an example embodiment of a medical-imaging system that illustrates additional details of a probe-interface subsystem. The medical-imaging system 10 includes an imaging station 100, an imaging subsystem 350, and a display device 500. The imaging subsystem 350 includes a bendable optical-imaging device 201, a patient interface unit (PIU) 202, and a probe-interface subsystem 300. The probe-interface subsystem 300 includes an OCT-light source 301, a splitter 302, a first circulator 303, a mirror 304, a second circulator 305, an OCT combiner 306, an OCT detector 307, an excitation-light source 310, a dichroic filter 311, a line filter 312, and a fluorescence detector 313. And the imaging station 100 includes an OCT-processing unit 110, a fluorescence-processing unit 120, and an X-ray-processing unit 130, which is in communication with another imaging station or an X-ray detector (e.g., to receive second detection data, to receive X-ray images). The OCT-processing unit 110, the fluorescence-processing unit 120, and the X-ray-processing unit 130 may be realized by one or more processors that implement computer-executable instructions or by other hardware (e.g., specially-configured circuitry).

This embodiment of the medical-imaging system 10 is a multi-modal optical coherence tomography (MMOCT) system (e.g., a multi-modality swept-source OCT system). Although this embodiment of the medical-imaging system 10 can perform both OCT imaging and fluorescence imaging (e.g., auto-fluorescence imaging, near-infrared auto-fluorescence imaging, fluorescence-lifetime imaging), some embodiments of the medical-imaging system 10 perform other modalities of imaging (e.g., near infrared spectroscopy (NIRS), ultrasound (such as intravascular ultrasound (IVUS))) in addition to fluorescence imaging and OCT imaging or in alternative to either or both of fluorescence imaging and OCT imaging.

In FIG. 4, the bendable optical-imaging device 201 includes a tubular flexible body (e.g., a catheter) that surrounds an optical probe. The tubular flexible body may be referred to herein as a "flexible body." Some embodiments of the bendable optical-imaging device 201 include one or more optical fibers (e.g., a single clad fiber, a double clad fiber (DCF)) with a polished ball lens at the tip thereof for side-view scanning. The distal optics of the bendable optical-imaging device 201 may also include a DCF, a GRIN lens, or a refractive element (e.g., grating).

Figure 5A:
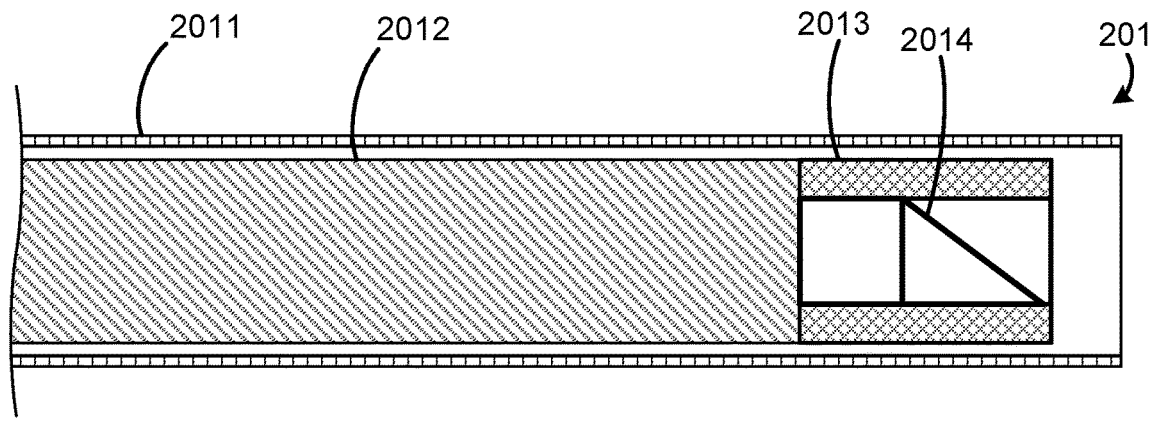
FIGS. 5A-B illustrate an example embodiment of a bendable optical-imaging device.
Figure 5B:
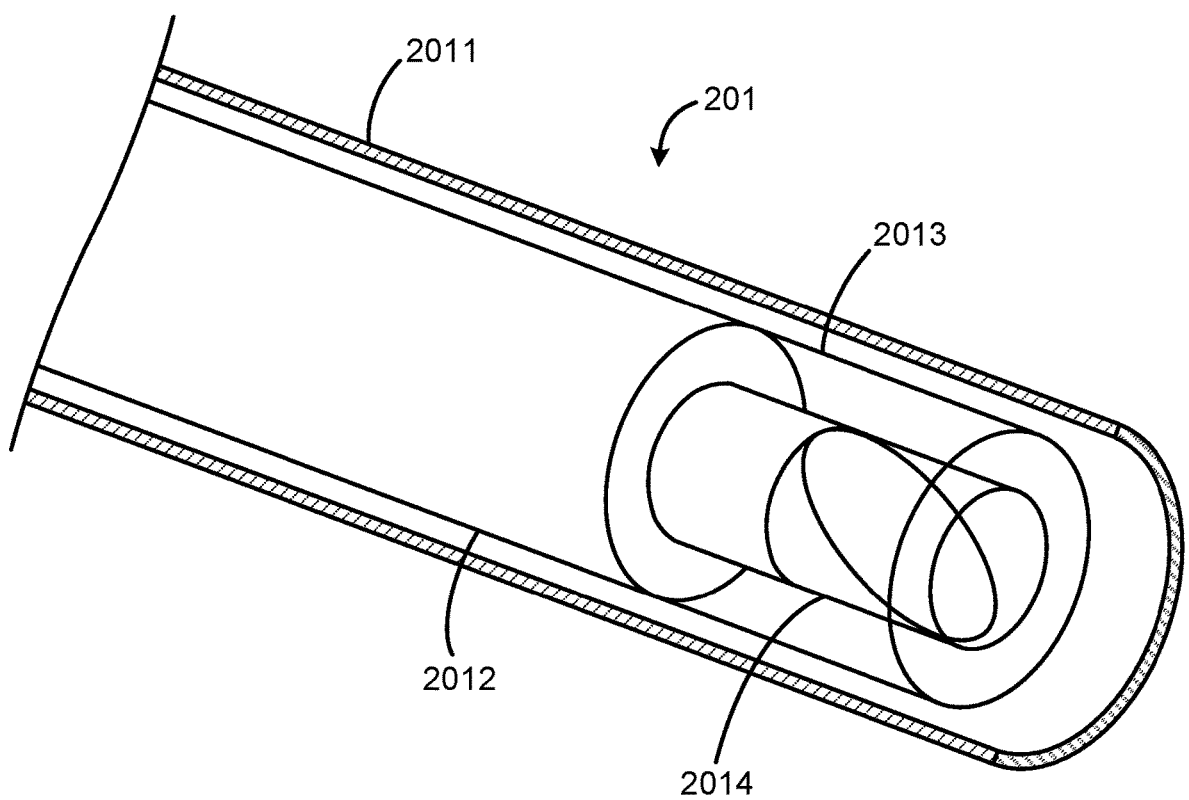

For example, FIGS. 5A-B illustrate an example embodiment of a bendable optical-imaging device. FIG. 5A illustrates a partially cutaway side view of the bendable optical-imaging device 201, and FIG. 5B illustrates a partially cutaway perspective view of the bendable optical-imaging device 201. The bendable optical-imaging device 201 includes a tubular flexible body 2011, a coil 2012, a protector 2013, and an optical probe 2014.

The bendable optical-imaging device 201 may be connected to the PIU 202, which can spin the coil 2012, for example during a pullback procedure. The coil 2012 delivers torque from its proximal end to its distal end. In some embodiments, the coil 2012 is fixed with, or to, the optical probe 2014 such that a distal end of the optical probe 2014 also spins with the coil 2012, which provides the optical probe 2014 with a panoramic or multidirectional view. As a beam of light travels through the optical probe 2014, the optical probe 2014 can be rotated, thereby providing the optical probe 2014 with multi-directional views of a surface of interest. Furthermore, the optical probe 2014 (as well as the rest of the bendable optical-imaging device 201) can simultaneously be translated longitudinally during the rotation, which produces a helical scanning pattern. This translation is commonly performed by pulling the distal end of the optical probe 2014 back towards the proximal end and is therefore referred to as a pullback procedure.

In some embodiments, the optical probe 2014 comprises an optical-fiber connector, an optical fiber, and a distal lens. The optical-fiber connector may be used to engage with the PIU 202, and the optical fiber may operate to deliver light to the distal lens and to deliver collected light from the distal lens to the PIU 202. For example, a DCF may transmit and collect OCT light that is reflected by a sample 601, and the DCF may transmit excitation light and collect Raman and fluorescence light that is reflected by the sample 601. The distal lens may shape the beam of light, direct illuminating light to the sample 601, and collect light that is reflected from the sample 601. The optical probe 2014 may also include a mirror at the distal end that deflects a beam of light outward.

Additionally, the PIU 202 includes a rotary junction 203 (e.g., a fiber-optic rotary junction (FORJ)), a beam combiner 204, and a pullback unit 205. During an optical-scanning procedure, the position of the optical probe 2014, as well as the rest of the bendable optical-imaging device 201, can be adjusted or controlled by the pullback unit 205. Some embodiments of the pullback unit 205 include a rotational motor and a translation motorized stage. In some embodiments, the rotary junction 203 is located in the pullback unit 205. The rotary junction 203 allows the optical probe 2014 to rotate inside the bendable optical-imaging device 201 and rotate relative to the PIU 202. During the rotation, which may be performed by the rotational motor, the optical probe 2014 (as well as the rest of the bendable optical-imaging device 201) can be moved longitudinally (e.g., by a translation motorized stage) so that light (e.g., OCT light, fluorescence light) is collected in a helical scanning pattern. For example, the rotation and translation movements can helically scan the optical probe 2014 inside a lumen and can produce a series of adjacent helical A-scans of the lumen, which can then be used to create a helical two-dimensional (2D) tomogram. Also for example, moving the optical probe 2014 longitudinally within the lumen allows the collection of a series of B-scans, which can be combined to form a three-dimensional (3D) image of the lumen.

The OCT-light source 301 generates OCT light (e.g., with a wavelength of approximately 1.3 µm), which is delivered to a splitter 302. The splitter 302 splits the OCT light into a reference arm $A_{ref}$ and a sample arm $A_{sam}$. The reference arm $A_{ref}$ includes the first circulator 303 and the mirror 304, and the sample arm $A_{sam}$ includes the bendable optical-imaging device 201 and the PIU 202. A reference beam of OCT light transmitted along the reference arm $A_{ref}$ is reflected by the mirror 304, is then transmitted to the first circulator 303, and is then transmitted to the OCT combiner 306. A sample beam of OCT light is transmitted through the second circulator 305, is transmitted along the sample arm $A_{sam}$ (through the one or more optical fibers of the bendable optical-imaging device 201), is incident on the sample 601 (e.g., an organ, tissue), and is reflected or scattered by the sample 601. Some of the reflected or scattered OCT light is collected by the bendable optical-imaging device 201, and the collected OCT light is transmitted through the bendable optical-imaging device 201 (through the one or more optical fibers of the bendable optical-imaging device 201), through the rotary junction 203, through the beam combiner 204 (which may separate the OCT light from the other collected light), and through the second circulator 305 to the OCT combiner 306.

In the OCT combiner 306, the OCT light from the reference arm $A_{ref}$ and the collected OCT light from the sample arm $A_{sam}$ are combined, thereby generating interference patterns. The combined light, which includes the interference patterns, is detected by the OCT detector 307 (e.g., a photodiode, a multi-array camera), which generates an OCT-detection signal $S_{1.1}$ that carries OCT-detection data based on the detected combined light. The OCT-detection signal $S_{1.1}$ is supplied to the OCT-processing unit 110 of the imaging station 100. The OCT-processing unit 110 obtains and processes the OCT-detection data.

Additionally, excitation light generated by an excitation-light source 310 is transmitted through the beam combiner 204 to the rotary junction 203, and then to the distal end of the bendable optical-imaging device 201, to illuminate the sample 601. In some embodiments, the excitation light has one of the following wavelengths or wavelength ranges: approximately 0.633 µm, 0.633-0.90 µm, and 0.500-0.700 µm. The excitation light incident on the sample 601 causes the sample 601 to emit fluorescence light. In some embodiments, the fluorescence light emitted by the sample 601 includes autofluorescence light, which is the endogenous fluorescence light that is generated without application of a dye or an agent. And the fluorescence light generated by the sample 601 may include fluorescence light generated by exogenous fluorescence dye or agent in the sample 601.

The bendable optical-imaging device 201 collects fluorescence light (e.g., autofluorescence light), Raman-scattered light, Brillouin-scattered light, and back-reflected excitation light (as well as OCT light) that are emitted or reflected by the sample 601. The one or more optical fibers carry the collected light to the proximal end of the bendable optical-imaging device 201.

After traveling through the beam combiner 204, the fluorescence light emitted from the sample 601, Raman-scattered light, Brillouin-scattered light, and back-reflected excitation light are supplied to a dichroic filter 311, which directs the fluorescence light to the fluorescence detector 313 (e.g., a photomultiplier tube (PMT)).

Also, this embodiment of the imaging subsystem 50 includes a line filter 312 (e.g., a laser line filer). The line filter 312 reduces signal washout from any remaining back-reflected excitation light that reaches the fluorescence detector 313. For example, the line filter 312 can be narrow with a high filtering capability for the NIRAF excitation wavelength (e.g., 635 nm), with only a couple of nanometers of bandwidth, or the bandwidth can be broader (e.g., up more than 2 nm and less than 20 nm or 40 nm) to reduce Raman signals from an optical fiber that can affect NIRAF signal-to-noise ratio.

Based on the received fluorescence light, the fluorescence detector 313 generates a fluorescence-detection signal $S_{1.2}$ that carries fluorescence-detection data that include detected values of the fluorescence light (detected fluorescence values). The detected fluorescence values may indicate the intensities of the detected fluorescence light. The fluorescence detector 313 provides the fluorescence-detection signal $S_{1.2}$, which carries the fluorescence-detection data, to the fluorescence-processing unit 120 of the imaging station 100. The fluorescence-processing unit 120 obtains and processes the fluorescence-detection data. In some embodiments, the OCT-detection signal $S_{1.1}$ and the fluorescence-detection signal $S_{1.2}$ are supplied to the imaging station 100 concurrently or simultaneously. Also, the OCT-detection signal $S_{1.1}$ and the fluorescence-detection signal $S_{1.2}$ may be included in a first detection signal $S_1$ that is supplied by the probe-interface subsystem 300 to the imaging station 100.

Figure 6:
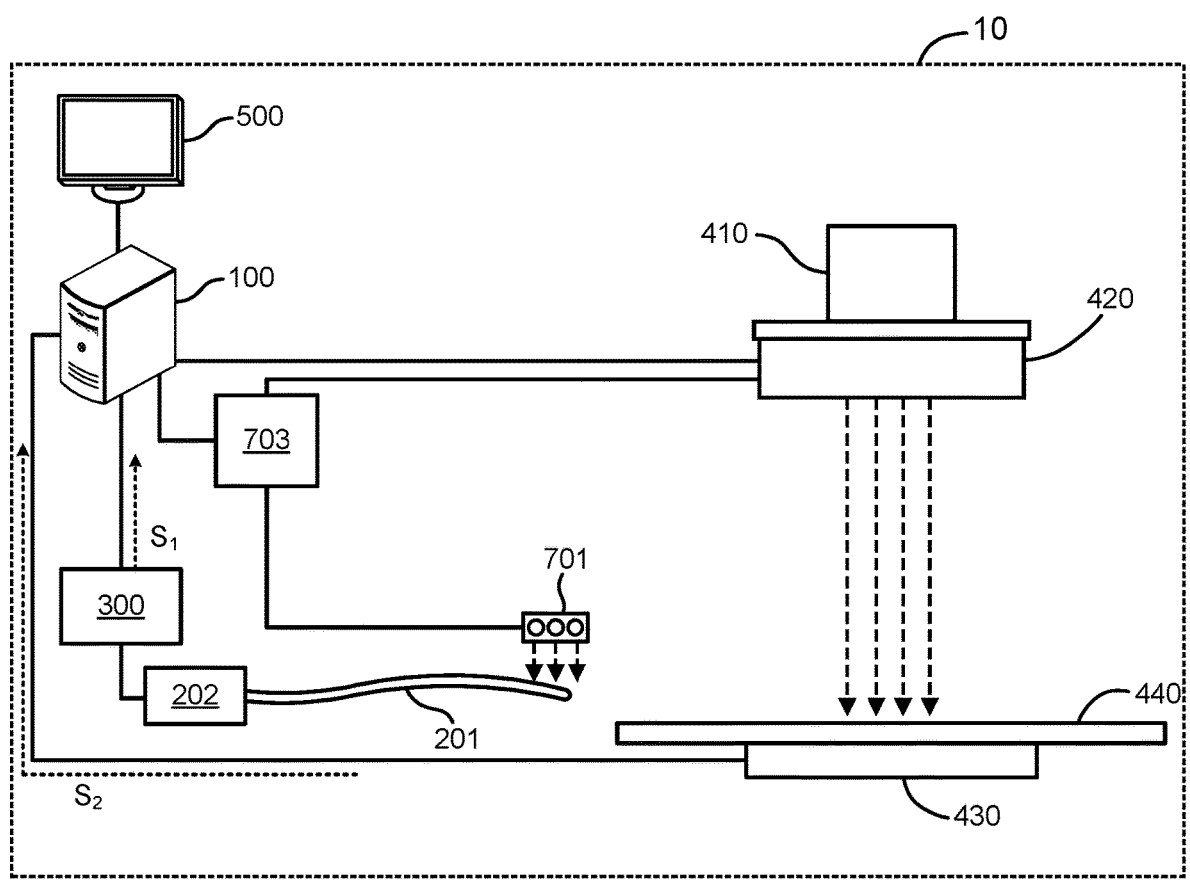
FIG. 6 is a schematic of an example embodiment of a medical-imaging system.

FIG. 6 is a schematic of an example embodiment of a medical-imaging system. This embodiment of a medical-imaging system 10 does not include an external shutter.

Instead, the timing-and-synchronization circuit 703 (which is controlled by the imaging station 100) controls the shutter (or shutters) in the beam-control device 420. Also, the imaging station 100 controls the bendable optical-imaging device 201, the PIU 202, the probe-interface subsystem 300, the X-ray generator 410, the beam-control device 420, the X-ray detector 430, the external light source 701, and the timing-and-synchronization circuit 703.

Figure 7:
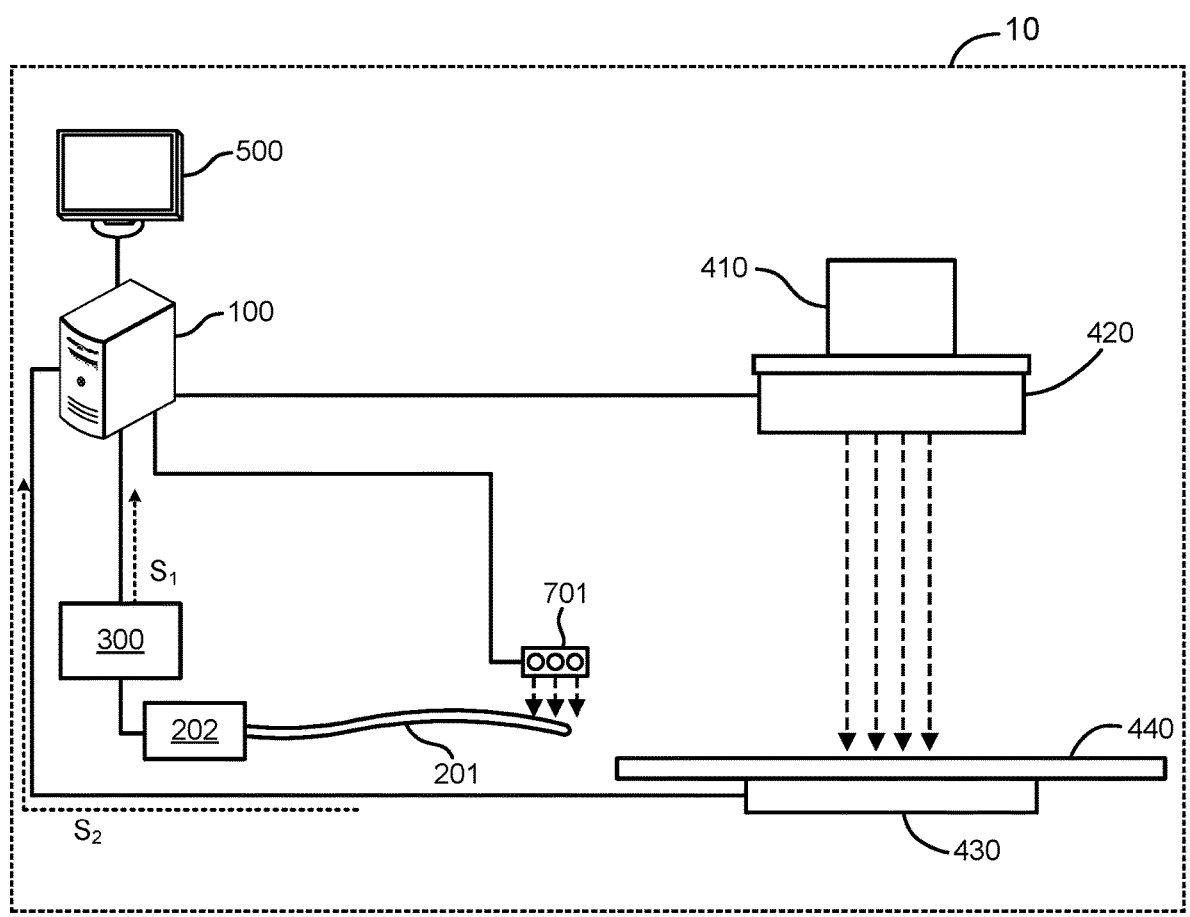
FIG. 7 is a schematic of an example embodiment of a medical-imaging system.

FIG. 7 is a schematic of an example embodiment of a medical-imaging system. In this embodiment of a medical-imaging system 10, the timing-and-synchronization circuit is included in the imaging station 100. Also, the imaging station 100 controls the bendable optical-imaging device 201, the PIU 202, the probe-interface subsystem 300, the X-ray generator 410, the beam-control device 420, the X-ray detector 430, and the external light source 701.

Figure 8:
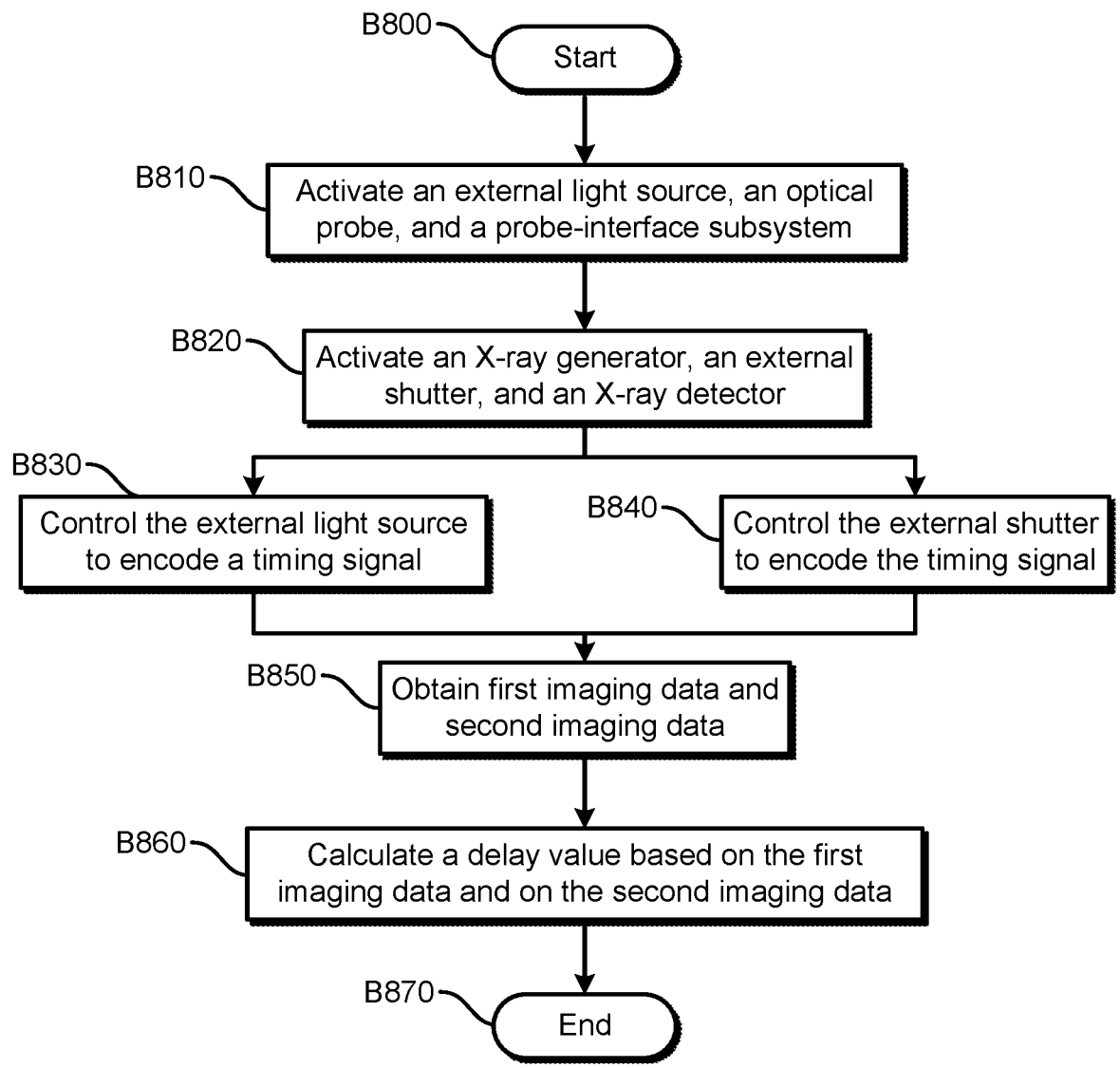
FIG. 8 illustrates an example embodiment of an operational flow for calculating a delay value.

FIG. 8 illustrates an example embodiment of an operational flow for calculating a delay value. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. And some embodiments of the operational flows may include blocks from two or more of the operational flows that are described herein. Thus, other embodiments of the operational flows that are described herein may omit blocks, add blocks, change the order of the blocks, combine blocks, or divide blocks into more blocks.

Furthermore, although some of the operational flows that are described herein are performed by an imaging station for simplicity of description, some embodiments of these operational flows are performed by two or more imaging stations or by one or more other specially-configured computing devices.

The flow begins in block B800 and moves to block B810, where an imaging station activates an external light source, an optical probe that has been positioned to detect light that is emitted by the external light source, and a probe-interface subsystem.

The flow then proceeds to block B820, where the imaging station activates an X-ray generator, an external shutter, and an X-ray detector that is positioned to detect X-rays that have passed through an opening in the external shutter. The flow then splits into a first flow and a second flow.

The first flow moves to block B830, where the imaging station controls the external light source to encode a timing signal. For example, the imaging station may instruct a timing-and-synchronization circuit to cause the external light source to pulse such that the light source emits light that has been modulated or interrupted to encode a timing signal. The optical probe, which is positioned to detect the light that is emitted by the external light source, detects the light that encodes the timing signal and generates first detection data based on the detected light. Accordingly, the first detection data also indicate (e.g., encode) the timing signal. The first flow then proceeds to block B850, where the first flow rejoins the second flow.

And the second flow moves to block B840, where the imaging station controls the external shutter to encode the timing signal. For example, the imaging station may instruct a timing-and-synchronization circuit to cause the external shutter to pulse such that external shutter modulates or interrupts the X-rays that pass through the opening to encode the timing signal. The X-ray detector, which is positioned to detect the X-rays that have passed through the opening, detects the X-rays that encode the timing signal and generates second detection data based on the detected X-rays. Accordingly, the second detection data also indicate (e.g., encode) the timing signal. The second flow then proceeds to block B850, where the second flow rejoins the first flow.

Additionally, the imaging station synchronizes blocks B830 and B840 such that the timing signal encoded (e.g., carried, induced, embedded, inserted) in the light emitted by the external light source is synchronized with the timing signal encoded (e.g., carried, induced, embedded, inserted) in the X-rays.

Next, in block B850, the imaging station obtains (e.g., receives, acquires) first imaging data (e.g., a series of first imaging data) and obtains second imaging data (e.g., a series of second imaging data). Also, block B850 may be performed while blocks B830 and B840 are being performed.

The first imaging data include the first detection data or include optical-scanning images that were generated from the first detection data. Also, the second imaging data include the second detection data or include X-ray images that were generated from the second detection data.

In some embodiments, when obtaining the first imaging data, the imaging station acquires the first detection data and generates optical-scanning images based on the first detection data. Also, when obtaining the second imaging data, the imaging station acquires X-ray images that were generated by another device (e.g., another imaging station) based on second detection data. And, in some embodiments, when obtaining the first imaging data, the imaging station acquires optical-scanning images that were generated by another device (e.g., another imaging station). Additionally, in some embodiments, when obtaining the second imaging data, the imaging station acquires the second detection data and generates X-ray images based on the second detection data.

And the imaging station may add respective timestamps to the first imaging data (e.g., first detection data, optical-scanning images) that indicate when the first imaging data were acquired or, in cases where the first imaging data include optical-scanning images, may add timestamps to optical-scanning images that indicate when the optical-scanning images were generated (e.g., when generation was completed). In embodiments where the first imaging data include groups (e.g., sets) of first imaging data that are received at different times, the imaging station may add a respective timestamp to each group of first imaging data. Also, each group of first imaging data may include the first imaging data that were all captured during a respective sampling period (e.g., each group of first imaging data may include the first detection data that define a respective optical-scanning image).

Furthermore, the imaging station may add timestamps to the second imaging data that indicate when the second imaging data were acquired or, in cases where the second imaging data include X-ray images, may add timestamps to the X-ray images that indicate when the X-ray images were generated (e.g., when generation was completed). When the second imaging data include groups (e.g., sets) of second imaging data that are received or generated at different times, the imaging station may add a respective timestamp to each group of second imaging data. Also, each group of second imaging data may include the second imaging data that were all captured during a respective sampling period (e.g., each group of second imaging data may include the second detection data that define a respective X-ray image).

The flow then moves to block B860, where the imaging station calculates a delay value based on the first imaging data and on the second imaging data. In some embodiments, the imaging station detects (e.g., demodulates, identifies, extracts) the timing signal from the optical-scanning images and detects the timing signal from the X-ray images. Also, the optical-scanning images may be one-dimensional arrays of pixels or each of the optical-scanning images may be composed of a respective plurality of frames, each of which is a respective one-dimensional array of pixels, and the first detection data may describe the pixel values of the pixels even when the pixels have not been formed into an image. Furthermore, when the external light source is positioned near the optical probe, all of the pixels in an optical-scanning image may have identical or nearly identical pixel values. Thus, some embodiments of the imaging station demodulate the timing signal directly from the first detection data (i.e., without first generating optical-scanning images from the first detection data). For example, some embodiments demodulate the timing signal using only the first detection data that constitute a subset of the pixels in the optical-scanning images. Furthermore, using the timing signal helps to ensure that the differences in pixel values are not noise.

The imaging station may identify the pixels in each optical-scanning image that indicate the timing signal (which, as noted above, may be every pixel), and the imaging station may identify the pixels in each X-ray image that indicate the timing signal. In embodiments where the X-rays that encode the timing signal irradiate only a portion of the X-ray detector, the imaging station may identify the pixels that constitute the portion that is irradiated by those X-rays and thus indicate the timing signal. For example, the imaging station may identify pixels (pixel locations) in a series of X-ray images that have pixel values that have image-to-image differences that exceed a threshold. Thus, if the pixel values at a pixel at location 100,100 vary by more than a threshold from image to image in a series of X-ray images, then the imaging station would identify the pixel at location 100,100 as a pixel that indicates the timing signal.

Also, the X-ray detector may perform a sample-and-hold operation when generating the second detection data from the detected X-rays, and the probe-interface subsystem may also perform a sample-and-hold operation when generating the first detection data.

For example, X-ray images are generated in discrete values (one image (frame) at a time). However, when generating the second detection data for each X-ray image, the X-ray detector detects X-rays over a period of time. Thus, the X-rays for an X-ray image are not detected instantly, but rather are detected over a sampling period (e.g., 20-33.33 ms), which may be described by an exposure time.

The timing signal is encoded in the X-ray images by operation of the external shutter. When the shutter is open, the corresponding X-ray image includes a bright region, and when the shutter is closed, that region is dark in the corresponding X-ray image (the entire X-ray image may be dark). In some embodiments, each pixel value is represented by 8 bits of data, so each pixel value could have a value from 0 to 255. And, because only some pixels in the X-ray images may capture the timing signal, the imaging station may check a number of X-ray images for pixels that have pixel-value differences that are above a threshold to identify the pixels (e.g., groups of pixels, image regions) to check in all of the X-ray images for the timing signal. For example, in embodiments in which larger pixel values represent brighter regions, and where the average pixel value without the timing signal is x and has standard deviation of s, a threshold may be x−3*s. Any pixel value less than the threshold (x−3*s) would represent a pixel containing the timing signal. A group of such pixels together would indicate the timing signal is present in the x-ray image.

In a sample-and-hold operation, if the shutter is closed over the entire sampling period, then the irradiated pixels will be the darkest possible (e.g., have a pixel value of 0). Also, if the shutter is open over the entire sampling period, then the irradiated pixels will be the lightest possible (e.g., have a pixel value of 255). And, if the shutter is open for half of the sampling period and is closed for the other half, then the resulting pixel values will be between the lightest and darkest values. For example, if the sampling period of the X-ray detector is 33.33 ms, and if the external shutter is open during the first half of the sampling period but closes halfway through (at 16.66 ms into the sampling period), and assuming that the closing operation requires 0 ms, then the external shutter is open during the first half of the sampling period and is closed during the second half. And each irradiated pixel will have a pixel value that is between the two extremes of the highest pixel value and the lowest pixel value. Also, a time value can be assigned to each pixel value using the timestamp that has been assigned to the X-ray image or the second detection data that include the pixel value. Thus, the imaging station can obtain a series of X-ray images (or second detection data) that encode the timing signal.

Similarly, the timing signal is encoded in the first detection data and the optical-scanning images by varying the light that is emitted by the external light source (e.g., by activating and deactivating the external light source).

Figure 9A:
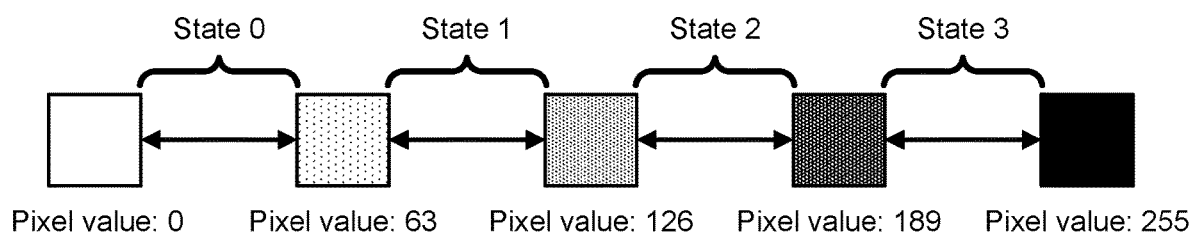
FIGS. 9A and 9B visually represent the mapping of pixel values to four states.
Figure 9B:
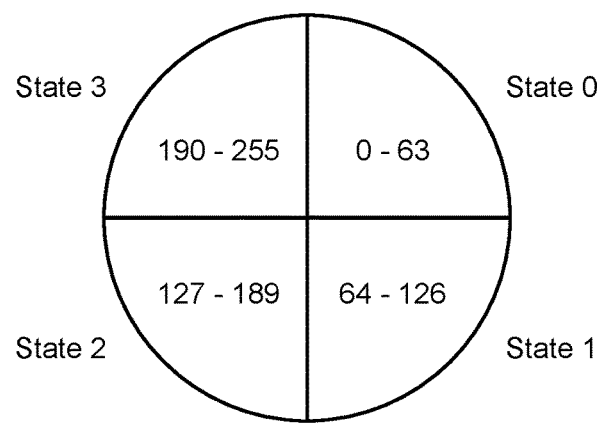

Various technologies and techniques can be used to encode and decode the timing signal. Examples include amplitude and phase-shift keying (APSK), quadrature amplitude modulation (QAM), chirp spread spectrum (CSS), and amplitude-shift keying (ASK). For example, some embodiments that encode the timing signal using ASK assign the pixel values to one of four different amplitudes, and the different amplitudes may represent discrete symbols, states, or values. For example, in some embodiments, the 256 possible values (from 0 to 255) are mapped to four different states. As an example, FIGS. 9A-B visually represent the mapping of pixel values to four states. In FIGS. 9A-B, the pixel values from 0-63 are mapped to state 0, the pixel values from 64-126 are mapped to state 1, the pixel values from 127-189 are mapped to state 2, and the pixel values from 190-255 are mapped to state 3. For a sample-and-hold period of 33.33 ms, these four states would give a maximum error in the calculated delay of 8.33 ms (33.33/4). And embodiments that use more states could decrease the maximum error. For example, embodiments that use 16 discrete states would have a maximum error in the calculated delay value of ~2 ms.

Also, some embodiments of imaging subsystems acquire optical-scanning images at a frame rate of 200 fps. A high-resolution pullback procedure may traverse a 50 mm linear distance with a frame rate of 200 fps (frames per second). Also, the velocity of the high-resolution pullback is 25 mm/s (millimeters per second); thus, the distance traveled in one optical-scanning image is approximately 0.125 mm. And a low resolution pullback may traverse an 80 mm linear distance with a frame rate of 30 fps.

Once the imaging station has demodulated the timing signal in the first detection data (or the optical-scanning images) and the timing signal in the X-ray images, the imaging station can calculate the delay value (e.g., $d_{disp2}-d_{disp1}$, $d_{rec2}-d_{rec1}$). The imaging station may use autocorrelation to match the timing signal in the first detection data (or the optical-scanning images) to the timing signal in the X-ray images. And example embodiments of the calculation of the delay value are described in FIGS. 13 and 14.

The imaging station then stores (or outputs) the delay value, and the flow ends in block B870. Also, the imaging station 100A may use the delay value to synchronize the display of optical-scanning images and X-ray images together on a display device 500 (or multiple display devices). For example, the imaging station may adjust the timing of the display of optical-scanning images according to the delay value, or the imaging station may adjust the timing of the display of X-ray images according to the delay value.

Figure 10:
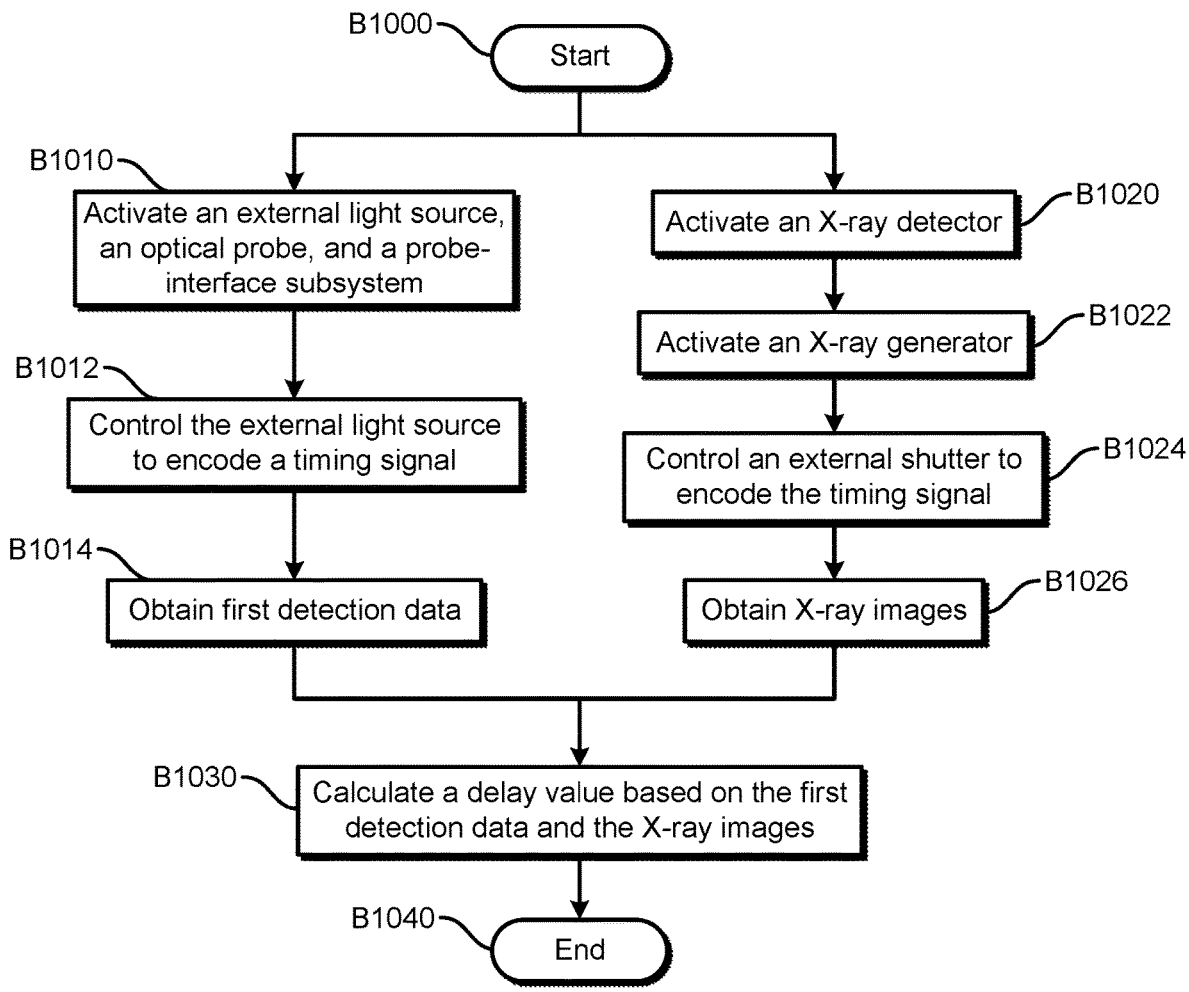
FIG. 10 illustrates an example embodiment of an operational flow for calculating a delay value.

FIG. 10 illustrates an example embodiment of an operational flow for calculating a delay value. The flow begins in block B1000 and then splits into a first flow and a second flow, which may be performed concurrently. The first flow proceeds to block B1010, where an imaging station activates an external light source, an optical probe that has been positioned to detect light that is emitted by the external light source, and a probe-interface subsystem. The first flow then moves to block B1012, where the imaging station controls the external light source to encode a timing signal (e.g., instructs a timing-and-synchronization circuit to cause the external light source to encode the timing signal) in the emitted light. And the first flow proceeds to block B1014, where the imaging station obtains first detection data. Also, blocks B1012 and B1014 may be performed concurrently. The first flow then advances to block B1030.

From block B1000, the second flow proceeds to block B1020. In block B1020, the imaging station activates an X-ray detector that is positioned to detect X-rays that have passed through an opening in an external shutter. Next, in block B1022, the imaging station activates an X-ray generator. And, in block B1024, the imaging station controls the external shutter to encode the timing signal (e.g., instructs a timing-and-synchronization circuit to cause the external shutter to encode the timing signal). Also, in block B1026, the imaging station obtains X-ray images (e.g., a series of X-ray images that were generated by another imaging station based on second detection data output by the X-ray detector). Additionally, blocks B1024 and B1026 may be performed concurrently. The second flow then moves to block B1030, where the second flow rejoins the first flow.

Furthermore, the imaging station (e.g., by using a timing-and-synchronization circuit) synchronizes blocks B1012 and B1024 such that the timing signal encoded in the light emitted by the external light source is synchronized with the timing signal encoded in the X-rays.

In block B1030, the imaging station calculates a delay value based on the first detection data and on the X-ray images, and the imaging station stores the calculated delay value.

Finally, the flow ends in block B1040.

Figure 11:
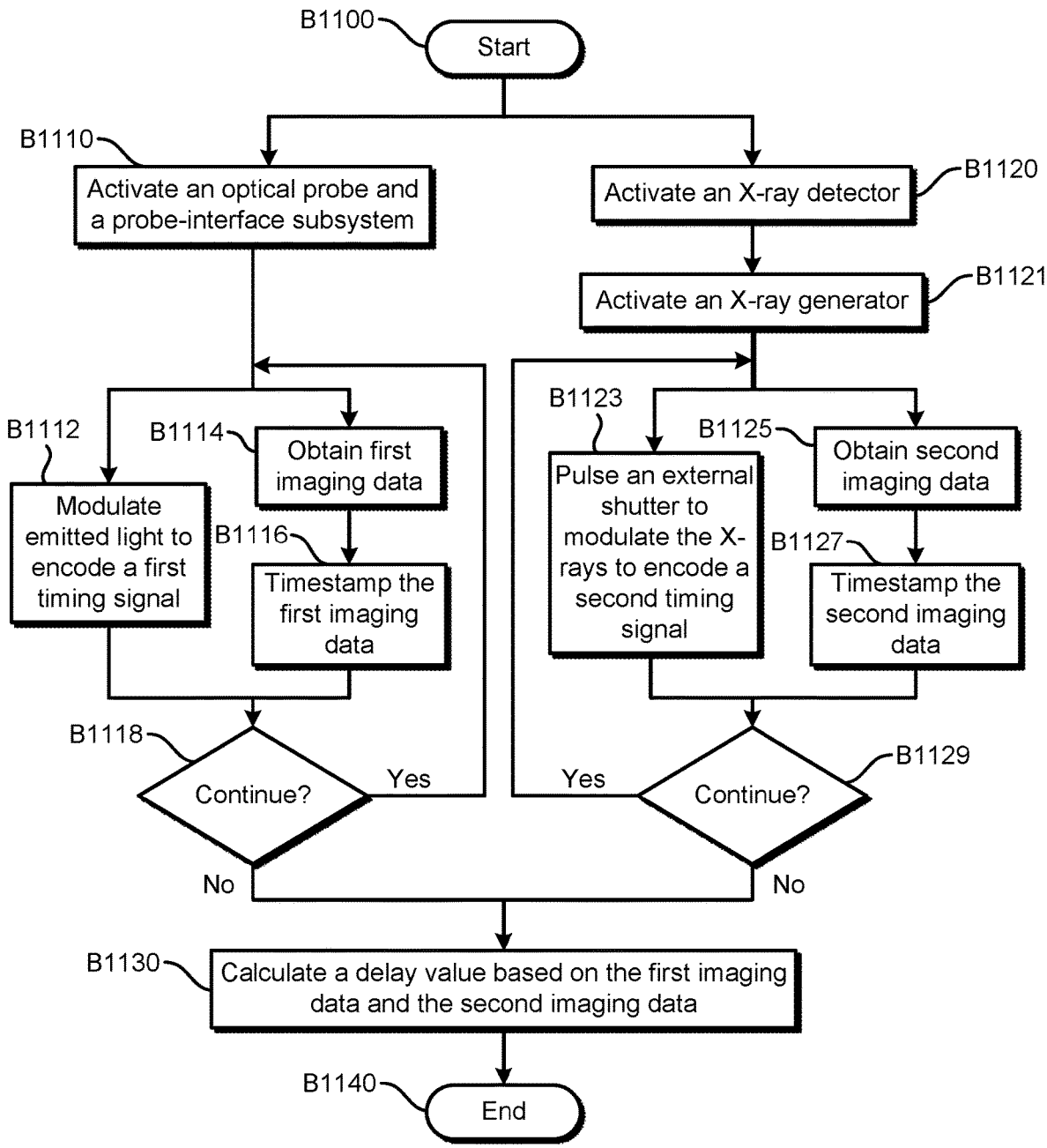
FIG. 11 illustrates an example embodiment of an operational flow for calculating a delay value.

FIG. 11 illustrates an example embodiment of an operational flow for calculating a delay value. The flow starts in block B1100 and then splits into a first flow and a second flow. The first flow progresses to block B1110, where an imaging station activates a probe-interface subsystem and an optical probe that has been positioned to detect light that is emitted by an external light source. The first flow then splits into a third flow and a fourth flow. The third flow moves to block B1112, where the imaging station controls the external light source to emit light that has been modulated to encode a first timing signal. The third flow then moves to block B1118, where it rejoins the fourth flow.

From block B1110, the fourth flow moves to block B1114, where the imaging station obtains first imaging data (e.g., a series of groups of first detection data, a series of optical-scanning images). Next, in block B1116, the imaging station timestamps the first imaging data. The timestamps may indicate when the first imaging data were received (e.g., when each group of first imaging data was received). The fourth flow then advances to block B1118, where it rejoins the third flow.

In block B1118, the imaging station determines whether to continue obtaining first detection data (e.g., whether the imaging station has been instructed to stop, whether a timer has expired, whether a count has been reached). If the imaging station determines to continue (B1118=Yes), then the first flow again splits into the third flow and the fourth flow, which return to blocks B1112 and B1114. If the imaging station determines not to continue obtaining first detection data (B1118=No), then the first flow proceeds to block B1130, where the first flow rejoins the second flow.

From block B1100, the second flow moves to block B1120, where the imaging station activates an X-ray detector that is positioned to detect X-rays that have passed through an opening in an external shutter. Next, in block B1121, the imaging station activates an X-ray generator. The second flow then splits into a fifth flow and a sixth flow. The fifth flow moves to block B1123, where the imaging station pulses the external shutter (e.g., by using a timing-and-synchronization circuit) to modulate the X-rays that pass through the external shutter such that these X-rays encode a second timing signal. Also, the first timing signal and the second timing signal may be identical. The fifth flow then proceeds to block B1129, where the fifth flow rejoins the sixth flow.

Furthermore, the imaging station (e.g., by using a timing-and-synchronization circuit) synchronizes blocks B1112 and B1123 such that the first timing signal is synchronized with the second timing signal or, alternatively, the first timing signal and the second timing signal have a known, fixed offset.

From block B1121, the sixth flow moves to block B1125, where the imaging station obtains second imaging data (e.g., second detection data, a series of X-ray images). The sixth flow then advances to block B1127, where the imaging station timestamps the second imaging data. And then the sixth flow rejoins the fifth flow in block B1129.

In block B1129, the imaging station determines whether to continue obtaining second detection data (e.g., whether the imaging station has been instructed to stop by a user, whether a timer has expired, whether a count has been reached). If the imaging station determines to continue (B1129=Yes), then the second flow again splits into the fifth flow and the sixth flow, which return to blocks B1123 and B1125. If the imaging station determines not to continue obtaining second detection data (B1129=No), then the second flow proceeds to block B1130, where the second flow rejoins the first flow.

In block B1130, the imaging station calculates a delay value based on the first imaging data (which include the timestamps that were added in block B1116) and on the second imaging data (which include the timestamps that were added in block B1127), and the imaging station stores or outputs the calculated delay value.

Finally, the flow ends in block B1140.

Figure 12:
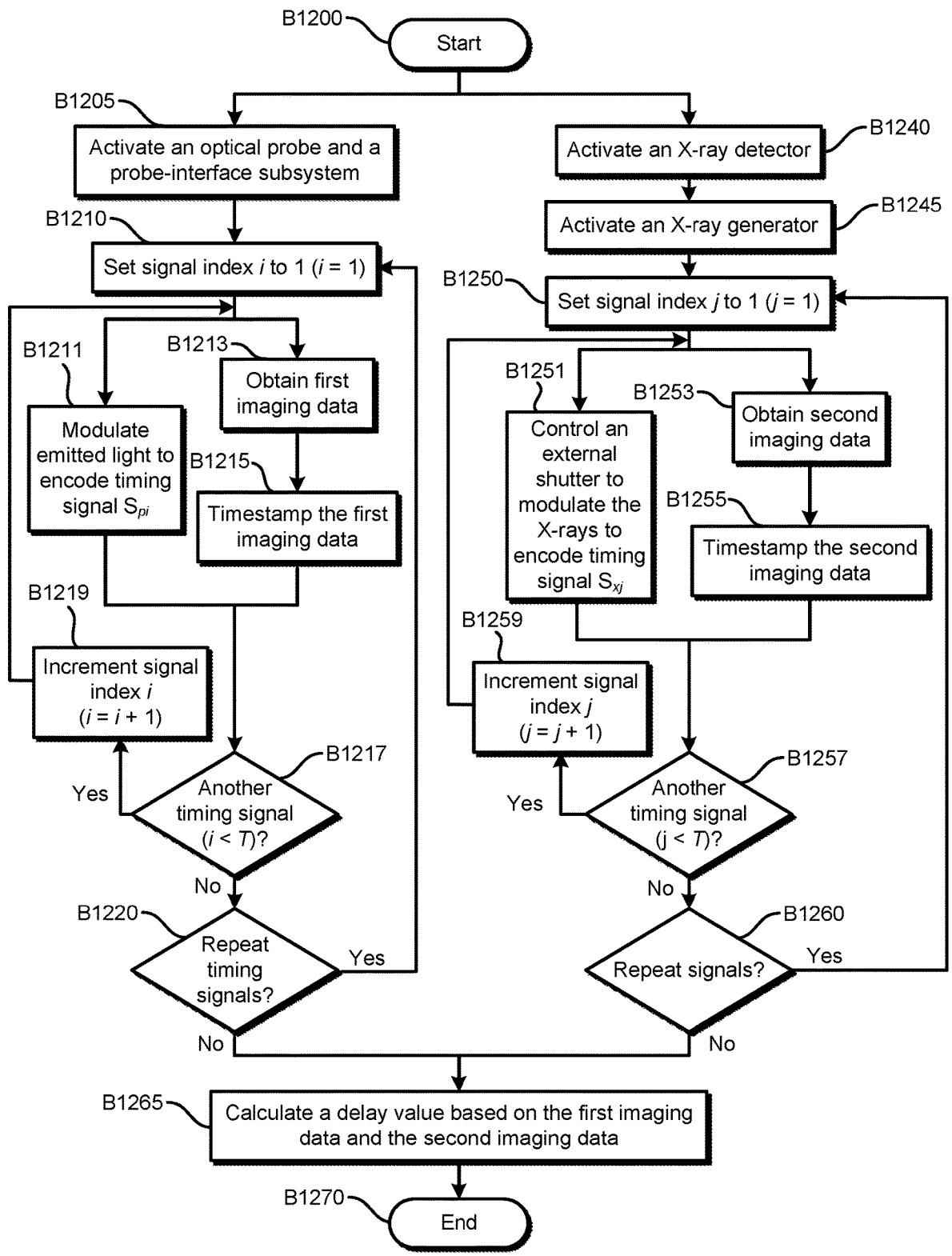
FIG. 12 illustrates an example embodiment of an operational flow for calculating a delay value.

FIG. 12 illustrates an example embodiment of an operational flow for calculating a delay value. The flow begins in block B1200 and then splits into a first flow and a second flow.

The first flow moves to block B1205, where an imaging station activates a probe-interface subsystem and an optical probe that has been positioned to detect light that is emitted by an external light source. Next, in block B1210, the imaging station sets a signal index i to 1 (i=1). The first flow then splits into a third flow and a fourth flow. The third flow proceeds to block B1211, where the imaging station controls an external light source to emit light that has been modulated to encode first timing signal $S_{pi}$. Then the third flow moves to block B1217, where the third flow rejoins the fourth flow.

From block B1210, the fourth flow moves to block B1213. In block B1213, the imaging station obtains first imaging data (e.g., first detection data, a series of optical-scanning images). Also, in block B1215, the imaging station timestamps the first imaging data as it is obtained. Thus, the imaging station may timestamp each group of first imaging data as it is obtained. The fourth flow then proceeds to block B1217, where it rejoins the third flow.

In block B1217, the imaging station determines whether to encode another timing signal. For example, in some embodiments, the imaging station has a series of T timing signals, where T is greater than 1, and at least some of the timing signals are different from other timing signals. Also, in some embodiments, T is one (and the imaging station may determine to repeat the one timing signal in block B1220). If the imaging station determines to encode another timing signal (B1217=Yes), then the first flow moves to block B1219, where the imaging station increments the signal index i by one (i=i+1). The first flow then splits into the third flow and the fourth flow, which return to blocks B1211 and B1213. If the imaging station determines not to encode another timing signal (B1217=No), then the first flow proceeds to block B1220.

In block B1220, the imaging station determines whether to repeat the timing signal or timing signals. For example, the imaging station may determine whether a stop instruction has been received or whether the timing signals have been encoded a certain number of times. If the imaging station determines to repeat the timing signal or the timing signals (B1220=Yes), then the first flow returns to block B1210. If the imaging station determines not to repeat the timing signals (B1220=No), then the first flow moves to block B1265, where the first flow rejoins the second flow.

From block B1200, the second flow proceeds to block B1240. In block B1240, the imaging station activates an X-ray detector. Then, in block B1245, the imaging station activates an X-ray generator. The second flow then advances to block B1250, where the imaging station sets signal index j to 1 (j=1). The second flow then splits into a fifth flow and a sixth flow. The fifth flow moves to block B1251, where the imaging station controls an external shutter to modulate the X-rays that are emitted by the X-ray generator such that the X-rays encode second timing signal $S_{xj}$. The fifth flow then moves to block B1257, where the fifth flow rejoins the sixth flow. Also, from block B1250 the sixth flow moves to block B1253, wherein the imaging station obtains second imaging data (e.g., second detection data, a series of X-ray images). And, in block B1255, the imaging station adds timestamps to the second imaging data as the imaging data are obtained. For example, the imaging station may add a timestamp to a group of second imaging data as it is obtained. Then the sixth flow advances to block B1257, where the sixth flow rejoins the fifth flow.

Furthermore, the imaging station synchronizes blocks B1211 and B1251 such that the timing signal encoded in the light emitted by the external light source is synchronized with the timing signal encoded in the X-rays or, alternatively, such that the timing signal encoded in the light emitted by the external light source and the timing signal encoded in the X-rays have a known, fixed offset.

In block B1257, the imaging station determines whether to encode another timing signal. If the imaging station determines to encode another timing signal (B1257=Yes), then the second flow moves to block B1259, where the imaging station increments the signal index j by one (j=j+1). The second flow then splits into the third flow and the fourth flow, which return to blocks B1251 and B1253. If the imaging station determines not to encode another timing signal (B1257=No), then the second flow proceeds to block B1260.

In block B1260, the imaging station determines whether to repeat the timing signal or timing signals. If the imaging station determines to repeat the timing signal or timing signals (B1260=Yes), then the second flow returns to block B1250. If the imaging station determines not to repeat the timing signals (B1260=No), then the second flow moves to block B1265, where the second flow rejoins the first flow.

In block B1265, the imaging station calculates a delay value based on the first imaging data (which include the timestamps that were added in block B1215) and the second imaging data (which include the timestamps that were added in block B1255), and the imaging station stores the calculated delay value. Finally, the flow ends in block B1270.

Additionally, in some embodiments, at least some of the third, fourth, fifth, and sixth flows are performed concurrently. Furthermore, the timing signals in the series of first timing signals $S_p$ may be identical to the timing signals in the series of second timing signals $S_x$. Thus, timing signal $S_{p1}$ may be identical to timing signal $S_{x1}$, timing signal $S_{p2}$ may be identical to timing signal $S_{x2}$, etc. Also, the timing signals may have known, fixed offsets.

Figure 13:
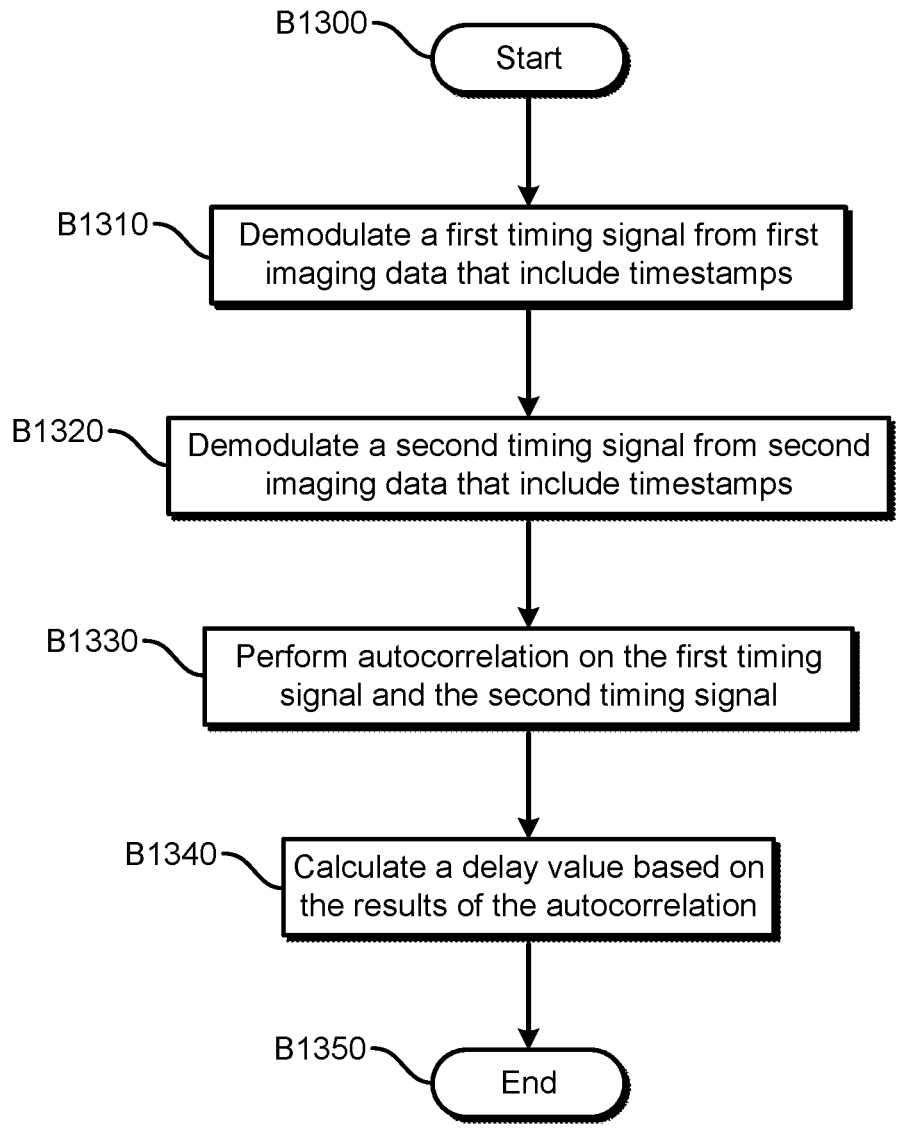
FIG. 13 illustrates an example embodiment of an operational flow for calculating a delay value using first and second imaging data.

FIG. 13 illustrates an example embodiment of an operational flow for calculating a delay value using first and second imaging data. The flow begins in block B1300 and then moves to block B1310, where an imaging station demodulates a first timing signal from first imaging data that include timestamps. For example, the imaging station may demodulate the first timing signal from first detection data that include timestamps, and the imaging station may demodulate the first timing signal from optical-scanning images that include timestamps. Also, in block B1310 the imaging station may perform an error-checking operation that includes performing an autocorrelation between the first timing signal that was demodulated from the first imaging data and the transmitted first timing signal (the first timing signal that was encoded in the light that was emitted by the external light source). If the two first timing signals do not adequately match, then the imaging station may return an error.

Next, in block B1320, the imaging station demodulates a second timing signal from second imaging data that include timestamps. For example, the imaging station may identify respective regions in a series of X-ray images that include the second timing signal and demodulate the second timing signal from the regions. Also, the imaging station may generate X-ray images from second detection data and then demodulate the second timing signal from the X-ray images. Additionally, in block B1320 the imaging station may perform an error-checking operation that includes performing an autocorrelation between the second timing signal that was demodulated from the second imaging data and the transmitted second timing signal (the second timing signal that was encoded in the X-rays). If the two second timing signals do not adequately match, then the imaging station may return an error.

The flow then moves to block B1330, where the imaging station performs autocorrelation (e.g., time-lagged cross correlation) on the first timing signal and the second timing signal. For example, some embodiments of the autocorrelation produce one or more root mean squared error. Also, the autocorrelation may directly compare the first and second timing signals to each other, and the autocorrelation may compare the first and second timing signals to another timing signal (e.g., a reference timing signal). Next, in block B1340, the imaging station calculates and stores a delay value based on the results of the autocorrelation.

Finally, the flow ends in block B1350.

Figure 14:
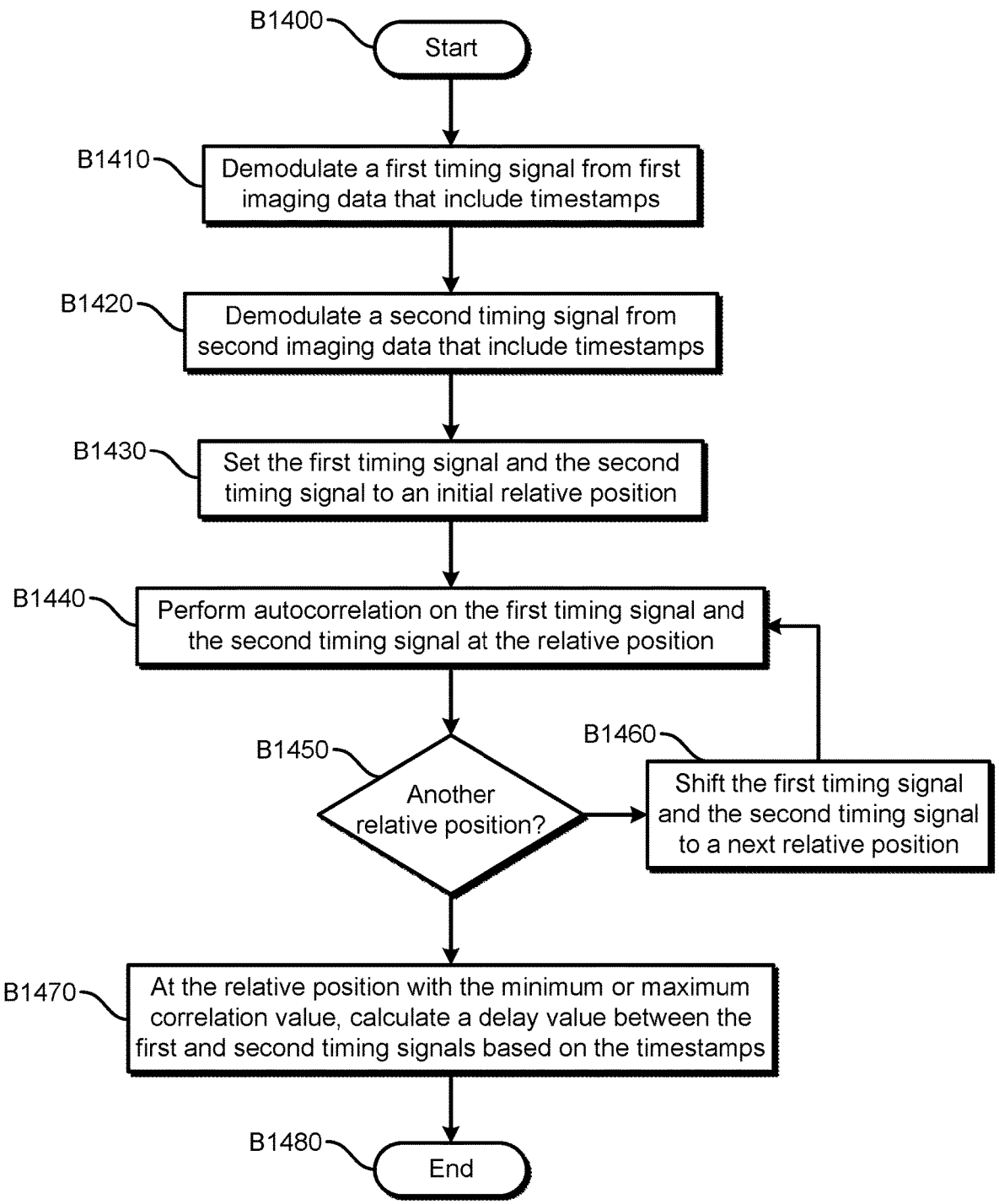
FIG. 14 illustrates an example embodiment of an operational flow for calculating a delay value using first and second imaging data.

FIG. 14 illustrates an example embodiment of an operational flow for calculating a delay value using first and second imaging data. The flow begins in block B1400 and then moves to block B1410, where an imaging station demodulates a first timing signal from first imaging data that include timestamps. Next, in block B1420, the imaging station demodulates a second timing signal from second imaging data that include timestamps.

The flow then moves to block B1430, where the imaging station sets the first timing signal and the second timing signal to an initial relative position. For example, in the initial relative position, the timestamps of the first timing signal may be aligned with the timestamps of the second timing signal. Or the timestamps of first and second timing signals may be offset by a time that is equal to a maximum search window (e.g., the second timing signal is shifted in time by a time that is equal to the maximum search window).

Then the flow proceeds to block B1440, where the imaging station performs an autocorrelation operation on the first timing signal and the second timing signal at the relative position, thereby generating one or more correlation values. For example, a correlation value may be the root mean squared error. Also, the imaging station may perform an autocorrelation operation on the first timing signal and a reference timing signal (e.g., a copy of the transmitted first timing signal) and perform an autocorrelation operation on the second timing signal and a reference timing signal (e.g., a copy of the transmitted second timing signal). For example, the imaging station may calculate the root mean squared error between the first timing signal and the copy of the transmitted first timing signal and calculate the root mean squared error between the second timing signal and the copy of the transmitted second timing signal. And the reference timing signals may be identical (e.g., the transmitted first timing signal may be identical to the transmitted second timing signal).

Next, in block B1450, the imaging station determines whether to perform block B1440 at another relative position. For example, the imaging station may determine whether a predetermined number of iterations have been performed or whether a certain search window (a range of time offsets) has been traversed. If the imaging station determines to perform block B1440 for another relative position (B1450=Yes), then the flow proceeds to block B1460, where the imaging station shifts the first timing signal and the second timing signal to a next relative position. For example, the imaging station may shift only the first timing signal by a set increment of time, and the imaging station may shift only the second timing signal by a set increment of time. The flow then returns to block B1440.

If the imaging station determines not to perform block B1440 for another relative position (B1450=No), then the flow proceeds to block B1470. In block B1470, at the relative position with the minimum or maximum correlation value (or sum of correlation values) the imaging station calculates a delay value between the first and second timing signals based on the timestamps. For example, at the relative position where the root mean squared error is the minimum, the imaging station may calculate a maximum difference of the differences between corresponding timestamps (timestamps that are aligned at the relative position) in the first and second timing signals. Also, the imaging station may calculate a minimum difference of the differences between corresponding timestamps in the first and second timing signals. And the imaging station may calculate an average difference of the differences between corresponding timestamps in the first and second timing signals.

Figure 15:
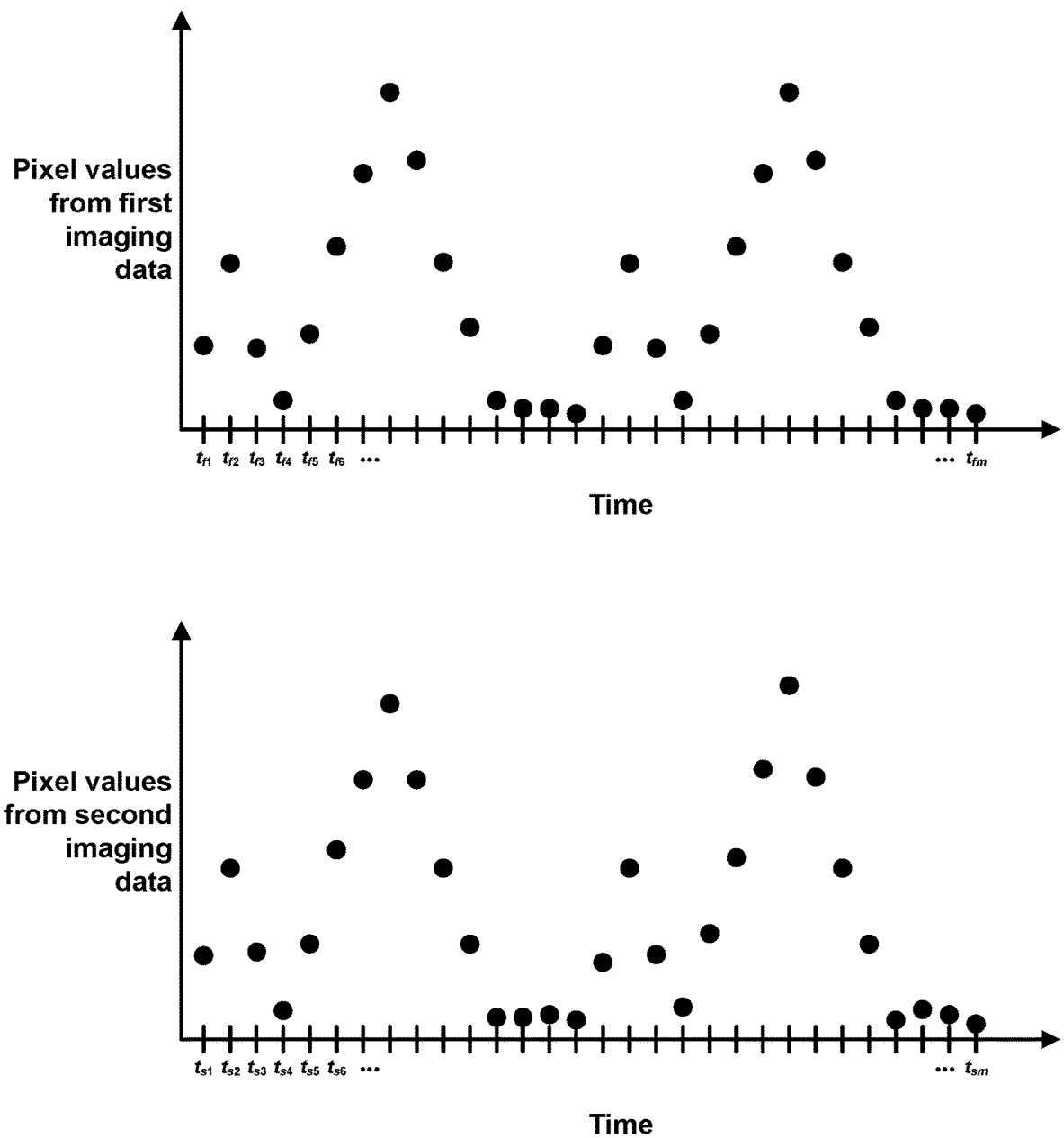
FIG. 15 illustrates an example embodiment of first and second timing signals.

For example, FIG. 15 illustrates an example embodiment of first and second timing signals. The upper graph in FIG. 15 shows the pixel values that were indicated by first imaging data, and these pixel values indicate the first timing signal. The lower graph shows the pixel values that were indicated by second imaging data, and these pixel values indicate the second timing signal. Also, the pixel values in the lower graph may have been identified as indicating the timing signal (e.g., by identifying respective regions, in series of X-ray images, that captured the timing signal). And the time value of each pixel value is the time value that is indicated by the pixel value's corresponding timestamp. Furthermore, although multiple pixels in the first imaging data and multiple pixels in the second imaging data may have pixel values that indicate the timing signal, for simplicity of description and illustration FIG. 15 shows the time-varying pixel values of only one pixel in the first imaging data and shows the time-varying pixel values of only one pixel in the second imaging data. However, the time-varying pixel values of other pixels in the first imaging data and the time-varying pixel values of other pixel in the second imaging data may also indicate the timing signal.

Furthermore, in this example, the graphs are aligned at the relative position of the minimum maximum correlation value (or the minimum maximum sum of correlation values). Thus, corresponding timestamps may not be equal. For example, in some embodiments timestamp $t_{f1}$ is not equal to corresponding timestamp $t_{s1}$, timestamp $t_{f2}$ is not equal to corresponding timestamp $t_{s2}$, timestamp $t_{f3}$ is not equal to corresponding timestamp $t_{s3}$, etc.

In some embodiments, the imaging station calculates all of the pairwise differences between the corresponding timestamps (e.g., calculates $|t_{fn} - t_{sn}|$ for n={1, 2, 3, 4, . . . m}, where m is the total number of timestamps) and sets the delay value to the minimum difference or, alternatively, to the maximum difference. Also, the imaging station may calculate the average of the pairwise differences between the corresponding timestamps and set the delay value to the average.

Finally, the flow ends in block B1480.

Figure 16:
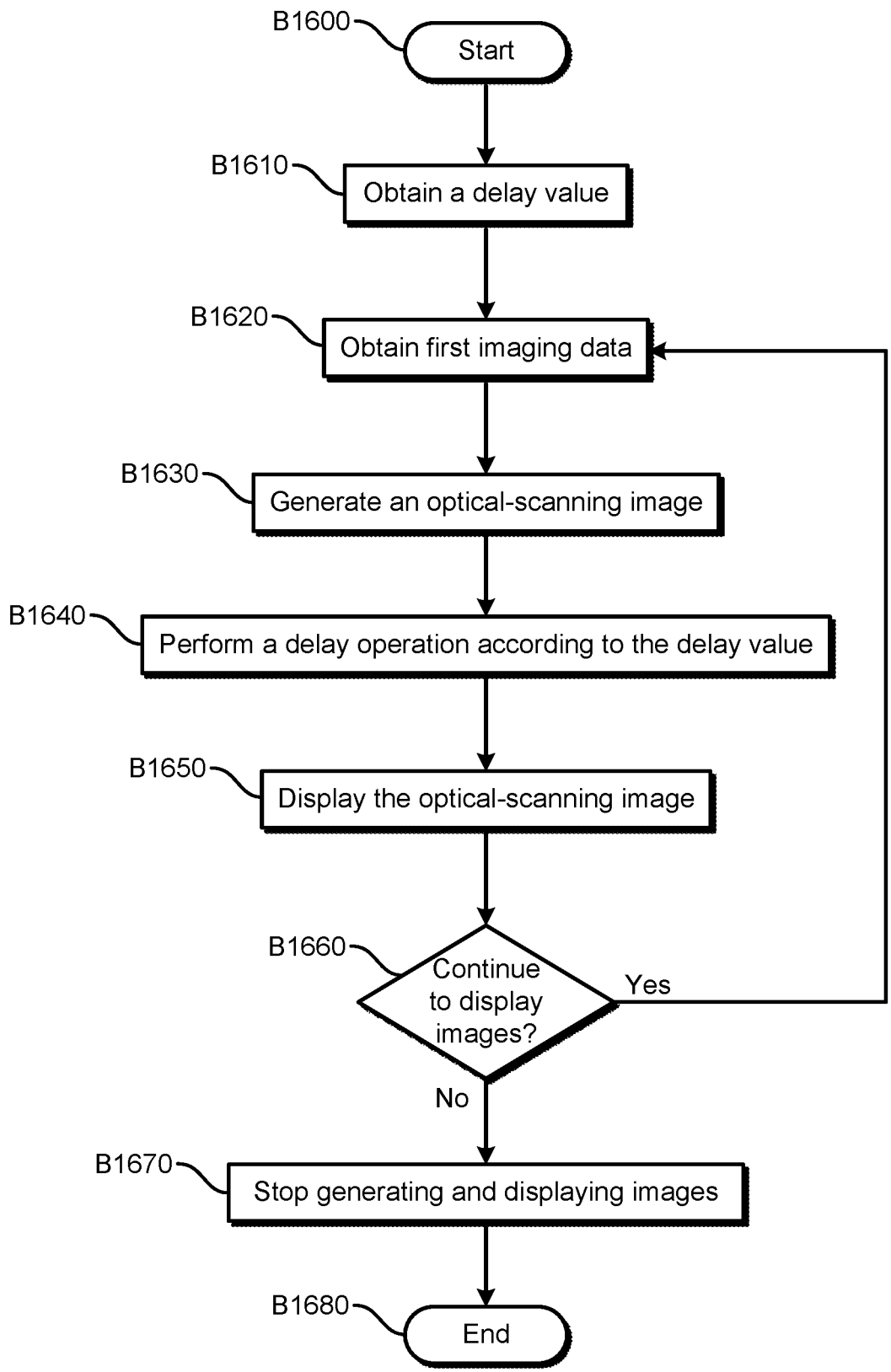
FIG. 16 illustrates an example embodiment of an operational flow for displaying images.

FIG. 16 illustrates an example embodiment of an operational flow for displaying images when the first optical-scanning image is available before the first X-ray image. The flow begins in block B1600 and then moves to block B1610, where an imaging station obtains a delay value (e.g., from memory, from storage, from another device). Then, in block B1620, the imaging station obtains first imaging data.

In embodiments in which the first imaging data include first detection data but not an optical-scanning image, the flow then moves to block B1630, where the imaging station generates an optical-scanning image based on the first detection data.

Next, in block B1640, the imaging station performs a delay operation. For example, the imaging station may wait for the amount of time that is indicated by the delay value before proceeding to block B1650. The flow then moves to block B1650, where the imaging station displays the optical-scanning image.

The flow then proceeds to block B1660, where the imaging station determines whether to continue to display images (e.g., whether a stop instruction has been received, whether reception of first or second imaging data has stopped, whether a set amount of time has passed). If the imaging station determines to continue (B1660=Yes), then the flow returns to block B1620. If the imaging station determines not to continue (B1660=No), then the flow moves to block B1670.

In block B1670, the imaging station stops generating and displaying images. And the flow ends in block B1680.

Figure 17:
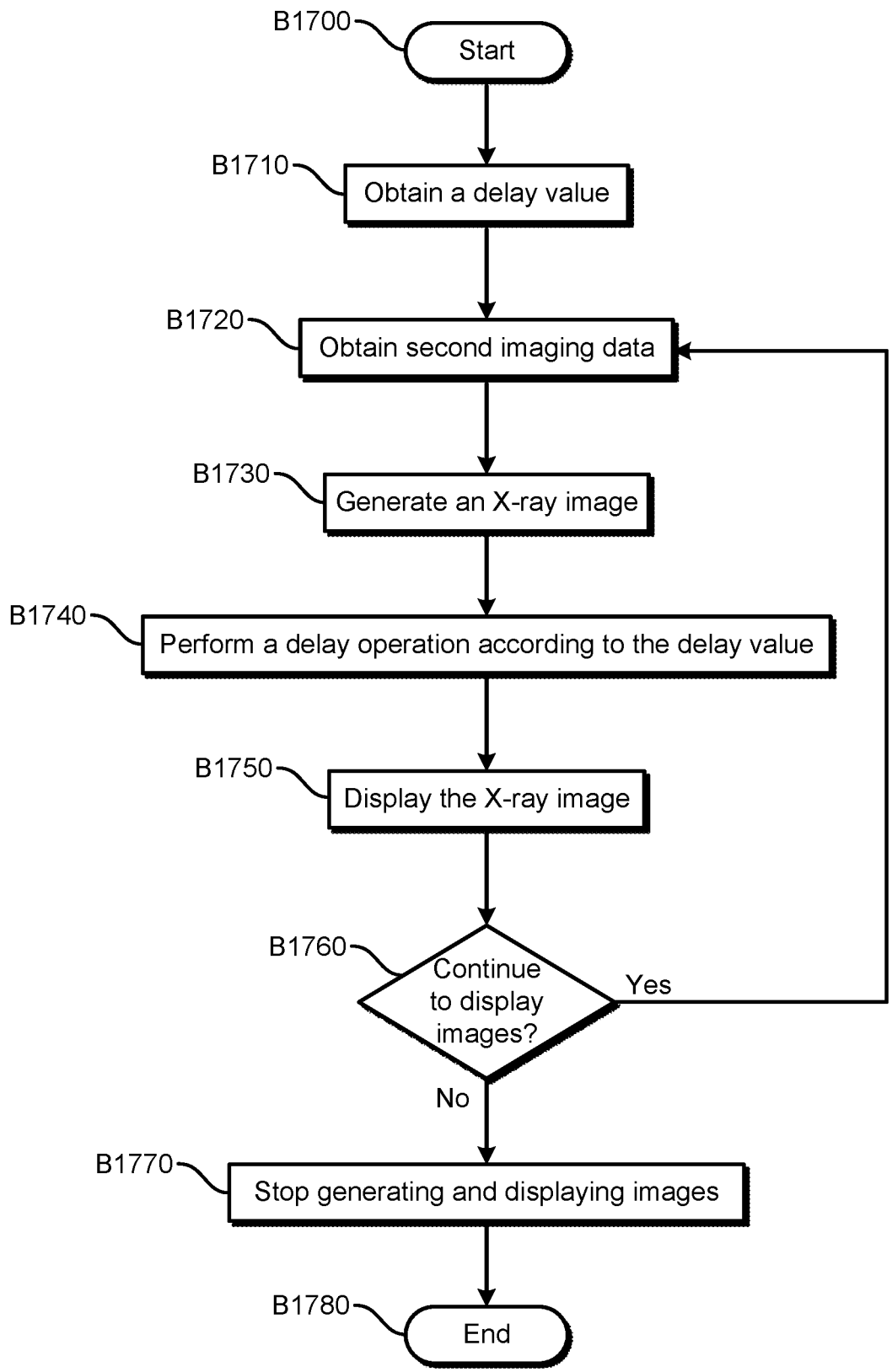
FIG. 17 illustrates an example embodiment of an operational flow for displaying images.

FIG. 17 illustrates an example embodiment of an operational flow for displaying images when the first X-ray scanning image is available before the first optical-scanning image. The flow begins in block B1700 and then moves to block B1710, where an imaging station obtains a delay value (e.g., from memory, from storage, from another device). Then, in block B1720, the imaging station obtains second imaging data.

In embodiments in which the second imaging data include second detection data but not an X-ray image, the flow then moves to block B1730, where the imaging station generates an X-ray image based on the second detection data.

Next, in block B1740, the imaging station performs a delay operation. For example, the imaging station may wait for the amount of time that is indicated by the delay value before proceeding to block B1750. The flow then moves to block B1750, where the imaging station displays the X-ray image.

The flow then proceeds to block B1760, where the imaging station determines whether to continue to display images (e.g., whether a stop instruction has been received, whether reception of first or second imaging data has stopped, whether a set amount of time has passed). If the imaging station determines to continue (B1760=Yes), then the flow returns to block B1720. If the imaging station determines not to continue (B1760=No), then the flow moves to block B1770.

In block B1770, the imaging station stops generating and displaying images. And the flow ends in block B1780.

Figure 18:
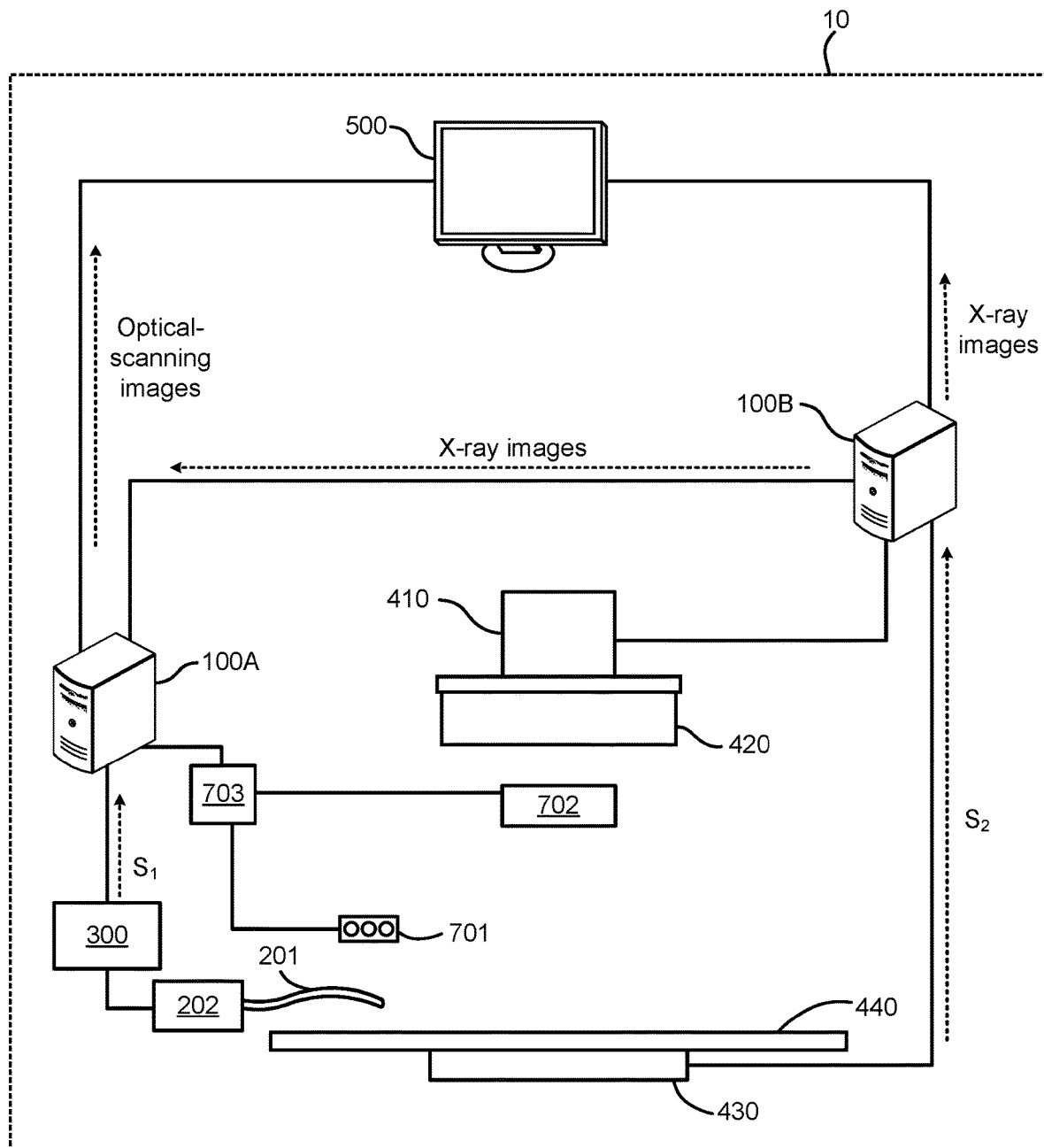
FIG. 18 is a schematic of an example embodiment of a medical-imaging system.

FIG. 18 is a schematic of an example embodiment of a medical-imaging system. The embodiment of the system 10 in FIG. 18 is similar to the embodiment in FIG. 1, and consequently descriptions of similar and identical components are omitted. However, in FIG. 18, both the first imaging station 100A and the second imaging station 100B send images (optical-scanning images and X-ray images) to a single display device 500. By using one or more calculated delay values, the first imaging station 100A and the second imaging station 100B can synchronize the display of the optical-scanning images and X-ray images on the single display device 500.

Figure 19:
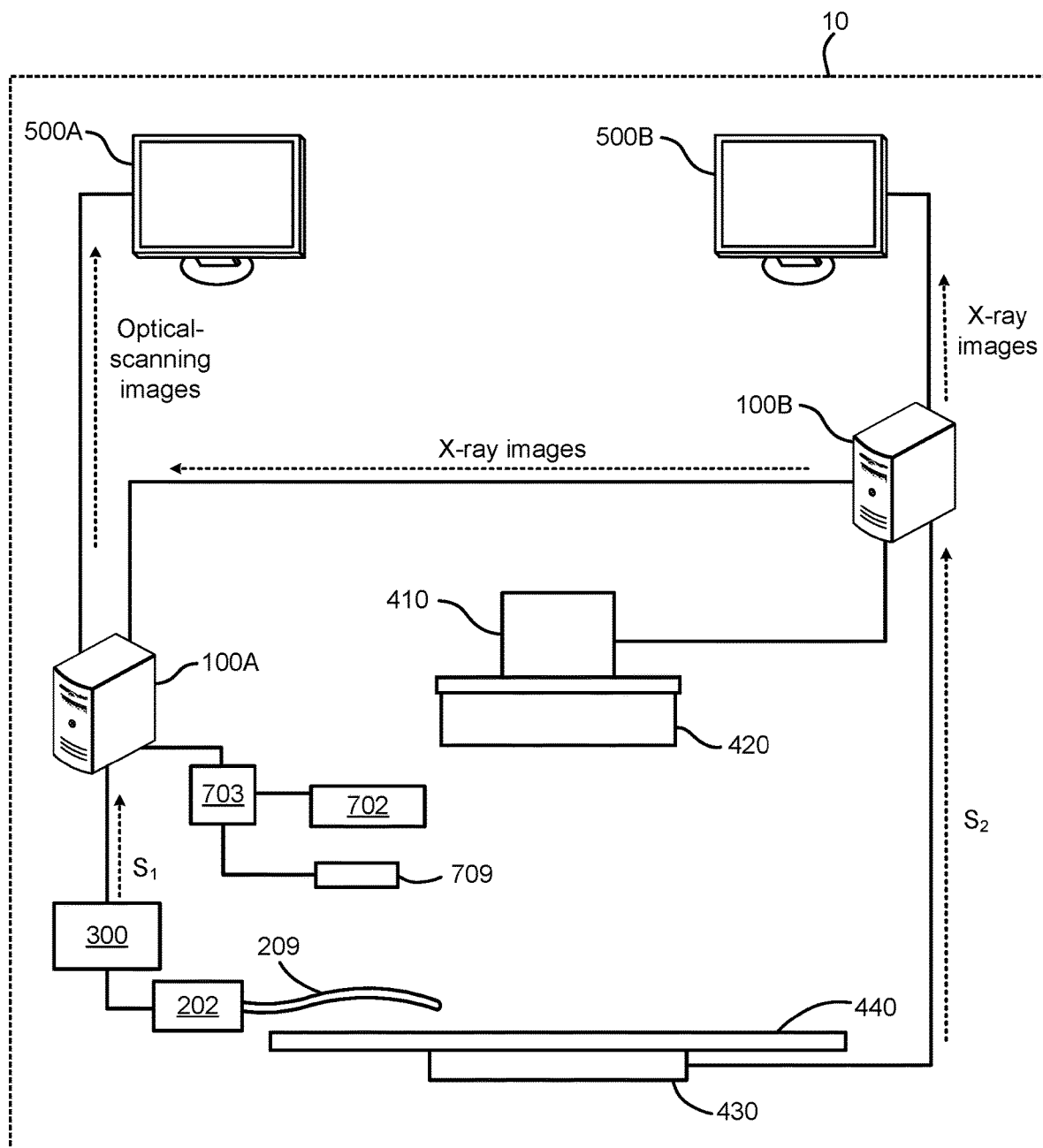
FIG. 19 is a schematic of an example embodiment of a medical-imaging system.

FIG. 19 is a schematic of an example embodiment of a medical-imaging system. The embodiment of the system 10 in FIG. 19 is similar to the embodiment in FIG. 1, and consequently descriptions of similar and identical components are omitted. However, in FIG. 19, the bendable optical-imaging device 201 is replaced by a bendable imaging device 209 that is configured for ultrasound imaging (e.g., intravascular ultrasound (IVUS) imaging), and the external light source 701 is replaced by an external ultrasonic emitter 709. Additionally, the probe-interface subsystem 300 is configured for ultrasound imaging. Furthermore, in some embodiments the PIU 202 and the bendable imaging device 209 are replaced by another type of ultrasonic probe. Furthermore, some embodiments of the system 10 may use other modalities of imaging, such as photoacoustic imaging.

For the embodiments that use an external ultrasonic emitter 709 instead of an external light source 701, the operations in the foregoing operational flows (e.g., in FIGS. 8, 10, 11, 12, 13, 14, and 16) replace the external light source with the external ultrasonic emitter 709, replace the bendable optical-imaging device 201 with a bendable imaging device 209 that is configured for ultrasound imaging or with another type of ultrasonic probe, and replace optical-scanning images with ultrasound images. Also, in such embodiments, the first detection data include ultrasonic detection data, and the first imaging data include ultrasonic detection data or ultrasound images. And similar changes can be made for other imaging modalities (e.g., photoacoustic imaging).

Furthermore, instead of replacing the optical-scanning components with the ultrasound components, some embodiments of the system 10 replace the X-ray components with the ultrasound components (or the components for other imaging modalities). Thus, some embodiments of the system 10 include a bendable optical-imaging device 201, a bendable imaging device 209 that is configured for ultrasound imaging, an external light source 701, an external ultrasonic emitter 709, a probe-interface subsystem 300 that is configured to optical-scanning images, and a probe-interface subsystem 300 that is configured for ultrasound imaging.

Figure 20:
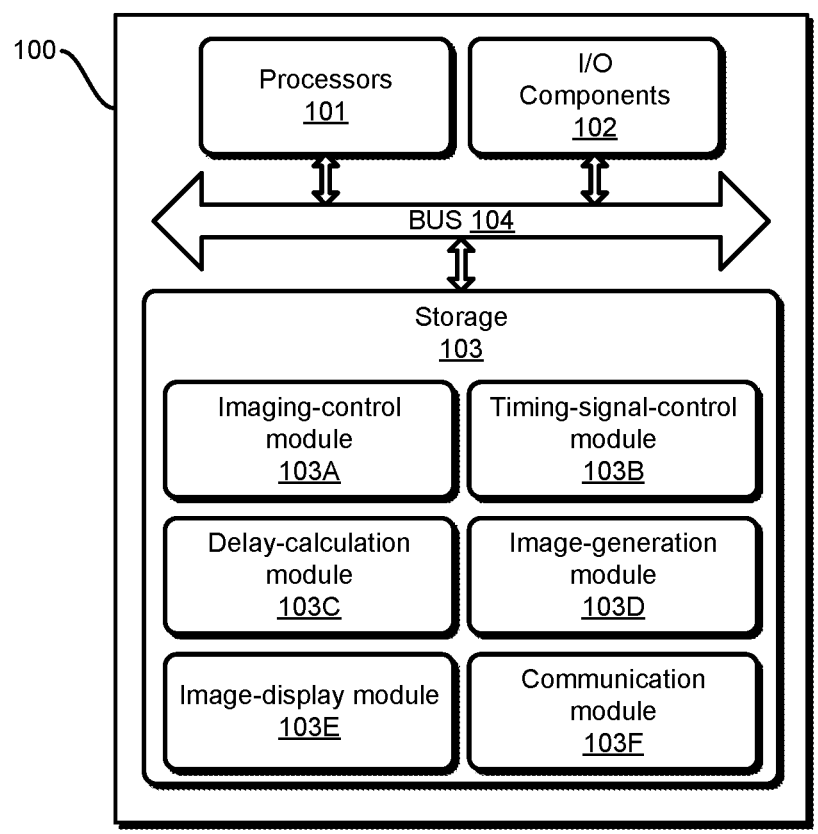
FIG. 20 illustrates an example embodiment of an imaging station.

FIG. 20 illustrates an example embodiment of an imaging station. The imaging station 100 includes one or more processors 101, one or more I/O components 102, and storage 103. Also, the hardware components of the imaging station 100 communicate via one or more buses 104 or other electrical connections. Examples of buses 104 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 101 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 102 include communication components (e.g., a GPU, a network-interface controller) that communicate with a display device, an imaging subsystem, a network, a timing-and-synchronization circuit, an X-ray detector, or other input or output devices (not illustrated), which may include a keyboard, a mouse, a printing device, a touch screen, a light pen, an optical-storage device, a scanner, a microphone, a drive, a joystick, and a control pad.

The storage 103 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 103, which may include both ROM and RAM, can store computer-readable data or computer-executable instructions.

The imaging station 100 additionally includes an imaging-control module 103A, a timing-signal-control module 103B, a delay-calculation module 103C, an image-generation module 103D, an image-display module 103E, and a communication module 103F. A module includes logic, computer-readable data, or computer-executable instructions. In the embodiment shown in FIG. 20, the modules are implemented in software (e.g., Assembly, C, C++, C #, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 103. Also, in some embodiments, the imaging station 100 includes additional or fewer modules, the modules are combined into fewer modules, or the modules are divided into more modules.

The imaging-control module 103A includes instructions that cause the imaging station 100 to control the operations of at least some of the following: an imaging subsystem, an X-ray generator, a beam-control device, and an X-ray detector. For example, some embodiments of the imaging-control module 103A include instructions that cause the imaging station 100 to perform at least some of the operations that are described in blocks B810, B830, and B850 in FIG. 8; in blocks B1010, B1014, B1020, B1022, and B1026 in FIG. 10; in blocks B1110, B1114, B1120, B1121, and B1125 in FIG. 11; in blocks B1205, B1213, B1240, B1245, and B1253 in FIG. 12; in block B1620 in FIG. 16; and in block B1720 in FIG. 17.

The timing-signal-control module 103B includes instructions that cause the imaging station 100 to control an external light source to modulate or interrupt emitted light to encode a timing signal, to control a shutter (e.g., an external shutter) to modulate or interrupt X-rays such that they encode a timing signal, or to control an external ultrasonic emitter to emit ultrasonic waves such that the ultrasonic waves encode a timing signal. For example, some embodiments of the timing-signal-control module 103B include instructions that cause the imaging station 100 to perform at least some of the operations that are described in blocks B820 and B840 in FIG. 8; in blocks B1012 and B1024 in FIG. 10; in blocks B1112, B1118, B1123, and B1129 in FIG. 11; and in blocks B1210, B1211, B1217, B1219, B1220, B1250, B1251, B1257, B1259, and B1260 in FIG. 12.

The delay-calculation module 103C includes instructions that cause the imaging station 100 to add timestamps to imaging data (e.g., first detection data, second detection data, optical-scanning images, X-ray images), to demodulate timing signals from imaging data, and to calculate one or more delay values. For example, some embodiments of the delay-calculation module 103C include instructions that cause the imaging station 100 to perform at least some of the operations that are described in block B1040 in FIG. 10, in block B1130 in FIG. 11, in block B1265 in FIG. 12, in blocks B1310-B1340 in FIG. 13, and in blocks B1410-B1470 in FIG. 14.

The image-generation module 103D includes instructions that cause the imaging station 100 to generate optical-scanning images from first detection data, to generate X-ray images from second detection data, or to generate ultrasound images or other modalities of images from detection data. For example, some embodiments of the image-generation module 103D include instructions that cause the imaging station 100 to perform at least some of the operations that are described in block B860 in FIG. 8, in block B1030 in FIG. 10, in block B1130 in FIG. 11, in block B1265 in FIG. 12, in blocks B1310 and B1320 in FIG. 13, in block B1630 in FIG. 16, and in block B1730 in FIG. 17.

The image-display module 103E includes instructions that cause the imaging station 100 to display optical-scanning images, to display X-ray images, or to display other modalities of images (e.g., ultrasound images). Also, the instructions may cause the imaging station 100 to delay the display of optical-scanning images, the display of X-ray images, or the display of the other modalities of images (e.g., ultrasound images) according to one or more delay values. For example, some embodiments of the image-display module 103E include instructions that cause the imaging station 100 to perform at least some of the operations that are described in blocks B1610, B1640, B1650, and B1660 in FIG. 16 and in blocks B1710, B1740, B1750, and B1760 in FIG. 17.

The communication module 103F includes instructions that cause the imaging station 100 to communicate with other devices.

The scope of the claims is not limited to the above-described embodiments and includes various modifications and equivalent arrangements.

The invention claimed is:

1. A device comprising:
one or more computer-readable media storing instructions; and
one or more processors that are in communication with the one or more computer-readable media and that, when executing the instructions, cooperate with the one or more computer-readable media to cause the device to perform operations that comprise:
obtaining first imaging data and first timestamps that correspond to the first imaging data, wherein the first imaging data include a first timing signal, and wherein the first timing signal, as included in the first imaging data, is encoded;
obtaining second imaging data and second timestamps that correspond to the second imaging data, wherein the second imaging data include a second timing signal, and wherein the second timing signal, as included in the second imaging data, is encoded;
demodulating the first imaging data to acquire the first timing signal as encoded in the first imaging data;
demodulating the second imaging data to acquire the second timing signal as encoded in the second imaging data; and
calculating a delay value based on the first timing signal as encoded in the first imaging data, the second timing signal as encoded in the second imaging data, the first timestamps, and the second timestamps, wherein calculating the delay value includes comparing a respective waveform of the first timing signal as encoded in the first imaging data with a respective waveform of the second timing signal as encoded in the second imaging data, wherein the respective waveform of the first timing signal is independent of any structure depicted in the first imaging data, and wherein the respective waveform of the second timing signal is independent of any structure depicted in the second imaging data.

2. The device of claim 1,
wherein the first timing signal was encoded by modulation that was performed according to the first timing signal as stored in one or more first memories that stored the first timing signal prior to the modulation that was performed according to the first timing signal, and
wherein the second timing signal was encoded by modulation that was performed according to the second timing signal as stored in one or more second memories that stored the second timing signal prior to the modulation that was performed according to the second timing signal.

3. The device of claim 2,
wherein the first timing signal was generated by a light source that output light and that modulated the output light, according to the first timing signal as stored in the one or more first memories, such that the output light, as modulated by the light source, encoded the first timing signal, and wherein the first imaging data capture the output light, and
wherein the second timing signal was generated by an X-ray shutter that modulated output X-rays, according to the second timing signal as stored in the one or more second memories, such that the output X-rays, as modulated by the X-ray shutter, encoded the second timing signal, wherein the second imaging data capture the output X-rays.

4. The device of claim 1, wherein a shape of the respective waveform of the first timing signal as encoded in the first imaging data is identical to a shape of the respective waveform of the second timing signal as encoded in the second imaging data.

5. The device of claim 2,
wherein the one or more computer-readable media include the one or more first memories and the one or more second memories, and
wherein the operations further comprise:
controlling a light source to modulate emitted light such that the emitted light, as modulated by the light source, encodes the first timing signal as stored in the one or more first memories or controlling an ultrasonic emitter to modulate emitted ultrasonic waves such that the emitted ultrasonic waves, as modulated by the ultrasonic emitter, encode the first timing signal as stored in the one or more first memories; and
controlling a shutter to modulate X-rays that travel through the shutter such that the X-rays that travel through the shutter, upon exiting the shutter, encode the second timing signal as stored in the one or more second memories,
wherein controlling the light source to modulate the emitted light or controlling the ultrasonic emitter to modulate the emitted ultrasonic waves is performed concurrently with controlling the shutter to modulate the X-rays that travel through the shutter.

6. The device of claim 1,
wherein the first imaging data were generated using a first imaging modality; and
wherein the second imaging data were generated using a second imaging modality that is different from the first imaging modality.

7. The device of claim 6, wherein the first imaging modality is optical-coherence-tomography imaging, fluorescence imaging, or ultrasound imaging; and
wherein the second imaging modality is X-ray imaging.

8. The device of claim 1,
wherein, prior to obtaining the first imaging data and prior to obtaining the second imaging data, the one or more computer-readable media store the first timing signal and the second timing signal; and
wherein the operations further comprise:
comparing the first timing signal as encoded in the first imaging data to the first timing signal as stored in the one or more computer-readable media prior to obtaining the first imaging data; and
comparing the second timing signal as encoded in the second imaging data to the second timing signal as stored in the one or more computer-readable media prior to obtaining the second imaging data.

9. The device of claim 1, wherein calculating the delay value based on the first timing signal and the second timing signal includes performing an autocorrelation operation on the first timing signal as encoded in the first imaging data and on the second timing signal as encoded in the second imaging data.

10. The device of claim 1, wherein the operations further comprise:
obtaining a series of images; and
for each image in the series of images, delaying display of the image according to the delay value, and then displaying the image.

11. A system comprising:
a light source;
a shutter;
one or more computer-readable media storing instructions; and
one or more processors that are in communication with the one or more computer-readable media, the light source, and the shutter, and that, when executing the instructions, cooperate with the one or more computer-readable media to perform operations that comprise:
controlling the light source to emit light such that the emitted light, upon emission from the light source, encodes a first timing signal; and
controlling the shutter such that X-rays travel through the shutter and such that, upon exiting the shutter, the X-rays that travel though the shutter encode a second timing signal,
wherein controlling the light source to emit light such that the emitted light encodes the first timing signal and controlling the shutter such that the X-rays that travel through the shutter, upon exiting the shutter, encode the second timing signal are performed concurrently.

12. The system of claim 11,
wherein the first timing signal as encoded in the emitted light is synchronized with the second timing signal as encoded in the X-rays that travel through the shutter.

13. The system of claim 11, wherein the operations further comprise:
obtaining first imaging data and first timestamps that correspond to the first imaging data, wherein the emitted light is captured using a first imaging modality, and wherein the first imaging data are generated from the emitted light that is captured using the first imaging modality;
obtaining second imaging data and second timestamps that correspond to the second imaging data, wherein the X-rays that travel through the shutter are captured using a second imaging modality, and wherein the second imaging data are generated from the X-rays that exit the shutter and that are captured using the second imaging modality;
demodulating the first imaging data to acquire the first timing signal as encoded in the first imaging data;
demodulating the second imaging data to acquire the second timing signal as encoded in the second imaging data; and
calculating a delay value based on the first timing signal as encoded in the first imaging data, the second timing signal as encoded in the second imaging data, the first timestamps, and the second timestamps.

14. The system of claim 13,
wherein the first timing signal is constituted by a first waveform,
wherein the second timing signal is constituted by a second waveform, and
wherein calculating the delay value includes comparing the first waveform as encoded in the first imaging data to the second waveform as encoded in the second imaging data.

15. The system of claim 13,
wherein the first timing signal is identical to the second timing signal, and
wherein calculating the delay value based on the first timing signal as encoded in the first imaging data, the second timing signal as encoded in the second imaging data, the first timestamps, and the second timestamps includes:
determining a relative timing position of the first timing signal as encoded in the first imaging data and the second timing signal as encoded in the second imaging data, and
calculating an average of pairwise differences between corresponding first and second timestamps, of the first timestamps and the second timestamps, at the relative timing position.

16. A method comprising:
obtaining first imaging data and a first series of timestamps that correspond to the first imaging data, wherein the first imaging data include a first timing signal, and wherein the first timing signal, as included in the first imaging data, is encoded;
obtaining second imaging data and a second series of timestamps that correspond to the second imaging data, wherein the second imaging data include a second timing signal, and wherein the second timing signal, as included in the second imaging data, is encoded;
demodulating the first imaging data to acquire the first timing signal as encoded in the first imaging data;
demodulating the second imaging data to acquire the second timing signal as encoded in the second imaging data; and
calculating a delay value based on the first timing signal as encoded in the first imaging data, the second timing signal as encoded in the second imaging data, the first series of timestamps, and the second series of timestamps, wherein the respective waveform of the first timing signal is independent of any structure depicted in the first imaging data, and wherein the respective waveform of the second timing signal is independent of any structure depicted in the second imaging data.

17. The method of claim 16,
wherein the first timing signal was encoded by modulation that was performed according to the first timing signal as stored in one or more first memories that stored the first timing signal prior to the modulation that was performed according to the first timing signal, and
wherein the second timing signal was encoded by modulation that was performed according to the second timing signal as stored in one or more second memories that stored the second timing signal prior to the modulation that was performed according to the second timing signal.

18. The method of claim 17, further comprising:
storing the first timing signal in the one or more first memories prior to the modulation that was performed according to the first timing signal;
storing the second timing signal in the one or more second memories prior to the modulation that was performed according to the second timing signal;
controlling a light source to modulate emitted light such that the emitted light, upon emission from the light source, encodes the first timing signal as stored in the one or more first memories, wherein the first imaging data capture the emitted light; and
controlling a shutter to modulate X-rays that travel through the shutter such that, upon exiting the shutter, the X-rays that travel though the shutter encode the second timing signal as stored in the one or more second memories, wherein the second imaging data capture the X-rays that travel through the shutter.

19. The method of claim 17, further comprising:
storing the first timing signal in the one or more first memories prior to the modulation that was performed according to the first timing signal;
storing the second timing signal in the one or more second memories prior to the modulation that was performed according to the second timing signal;
controlling an ultrasonic emitter to modulate emitted ultrasonic waves such that the emitted ultrasonic waves, upon emission from the ultrasonic emitter, encode the first timing signal as stored in the one or more first memories, wherein the first imaging data capture the emitted ultrasonic waves; and
controlling a shutter to modulate X-rays that travel through the shutter such that, upon exiting the shutter, the X-rays that travel though the shutter encode the second timing signal as stored in the one or more second memories, wherein the second imaging data capture the X-rays that travel through the shutter.

20. The method of claim 16, further comprising:
obtaining a series of images; and
for each image in the series of images, delaying display of the image according to the delay value, and then displaying the image.

\* \* \* \* \*